(12) United States Patent
Gheeraert et al.

(10) Patent No.: US 10,357,205 B2
(45) Date of Patent: *Jul. 23, 2019

(54) ELECTROCARDIOGRAM ANALYSIS

(71) Applicant: UNIVERSITEIT GENT, Ghent (BE)

(72) Inventors: Peter Gheeraert, Gentbrugge (BE); Milad El Haddad, Vantaa (FI)

(73) Assignee: UNIVERSITEIT, Ghent (BE)

(*) Notice: Subject to any disclaimer, the term of this patent is extended or adjusted under 35 U.S.C. 154(b) by 0 days.

This patent is subject to a terminal disclaimer.

(21) Appl. No.: 14/927,775

(22) Filed: Oct. 30, 2015

(65) Prior Publication Data

US 2016/0045166 A1 Feb. 18, 2016

Related U.S. Application Data

(63) Continuation-in-part of application No. PCT/EP2014/060766, filed on May 26, 2014.

(30) Foreign Application Priority Data

May 24, 2013 (EP) .................................... 13169090

(51) Int. Cl.
*A61B 5/04* (2006.01)
*A61B 5/00* (2006.01)
(Continued)

(52) U.S. Cl.
CPC .......... *A61B 5/7271* (2013.01); *A61B 5/0245* (2013.01); *A61B 5/0408* (2013.01);
(Continued)

(58) Field of Classification Search
CPC .......................... A61B 5/04011; A61B 5/0402
See application file for complete search history.

(56) References Cited

U.S. PATENT DOCUMENTS 6,038,469 A * 3/2000 Karlsson ............. A61B 5/0006
600/509
6,055,448 A 4/2000 Anderson et al.
(Continued)

FOREIGN PATENT DOCUMENTS

EP 1 214 905 A1 6/2002
EP 1214905 * 6/2002 ........... A61B 5/0432
(Continued)

OTHER PUBLICATIONS

Sederholm, Magnus et al., "Continuous vectorcardiography in acute myocardial infarction. Natural course of ST and QRS vectors", International Journal of Cardiology, Elsevier Science Publishers, Aug. 1, 1983, vol. 4, No. 1, pp. 53-56.
(Continued)

*Primary Examiner* — Eric D. Bertram
(74) *Attorney, Agent, or Firm* — Workman Nydegger

(57) ABSTRACT

A device is described for analyzing electrocardiogram data. The device comprises processing means for comparing at least one parameter derived from a temporal sequence of electrocardiogram data a previously recorded distribution of that parameter obtained from the user under a plurality of different physiological conditions. Based on the comparison, a signal representative of a risk of a myocardial infarction occurring in the body of the user is provided. A corresponding method, device and computer application for installing on a user device are also described.

25 Claims, 12 Drawing Sheets

(51) Int. Cl.
    *A61B 5/0452*     (2006.01)
    *A61B 5/0245*     (2006.01)
    *A61B 5/0408*     (2006.01)

(52) U.S. Cl.
    CPC ........ *A61B 5/04011* (2013.01); *A61B 5/0452* (2013.01); *A61B 5/04525* (2013.01); *A61B 5/6823* (2013.01); *A61B 5/7275* (2013.01)

(56) References Cited

U.S. PATENT DOCUMENTS

| | | |
|---|---|---|
| 9,867,577 B2 * | 1/2018 | Gheeraert ............ A61B 5/7282 |
| 2002/0188214 A1 | 12/2002 | Misczynski et al. |
| 2005/0085736 A1 | 4/2005 | Ambrose et al. |
| 2011/0152696 A1 | 6/2011 | Ryan |
| 2012/0179055 A1 | 7/2012 | Tamil et al. |

FOREIGN PATENT DOCUMENTS

| | | |
|---|---|---|
| WO | 2004/004560 A1 | 1/2004 |
| WO | 2014/187998 A1 | 11/2014 |

OTHER PUBLICATIONS

Exteneded European Search Report from EP Application No. 13169090.1, dated Oct. 28, 2013.

International Search Report from International PCT Application No. PCT/EP2014/060766, dated Aug. 13, 2014.

Tragardh-Johansson et al., "Similarity of ST and T Waveforms of 12-lead Electrocardiogram Acquired from Different Monitoring Electrode Positions", Science Direct, Journal of Electrocardiology, vol. 44, Issue 2, pp. 109-114, 2011.

* cited by examiner

ELECTROCARDIOGRAM ANALYSIS

FIELD OF THE INVENTION

The invention relates to the field of cardiovascular health risk management and disease detection. More specifically it relates to methods and devices for analyzing electrocardiogram data in order to determine a signal indicative of myocardial infarction, e.g. an alert state indicative of the detected occurrence of a possible ST-segment elevation myocardial infarction (STEMI) event using self-testing applications.

BACKGROUND OF THE INVENTION

The presence of a cardiovascular complication in a patient entails an important health risk, which forms one of the leading causes of morbidity and mortality in Europe and North America. A reliable diagnosis of such a cardiovascular complication has a significant impact on successful treatment, which is particularly important for patients showing symptoms of acute coronary syndrome (ACS), since such symptoms of ACS imply a heightened risk of experiencing irreversible cardiac injury. An acute coronary syndrome is caused by a blockage in a coronary artery which substantially cuts off the blood supply to connected areas of the myocardium, resulting in acute myocardial ischemia.

Patients with chest pain or signs of instable angina or ACS may frequently present to their doctor or to the emergency room for clinical evaluation, which includes evaluation of their medical history specifically directed to evidence of existing cardiovascular disease or risk factors therefor, analysis of the type of symptoms as described, as well as clinical signs associated with acute coronary syndrome such as evidence of pulmonary edema, hypotension, tachycardia or bradycardia. Furthermore, an electrocardiogram (ECG) and laboratory tests may be performed. From the evidence obtained, a diagnosis may be established which includes confirmation of the suspected ACS and a differential diagnosis for, for example, unstable angina pectoris (UAP), ST-segment elevation myocardial infarction (STEMI) or non-ST-segment elevation myocardial infarction (NSTEMI). Particularly, the ECG may provide important information for confirmation of ACS and differential diagnosis. The interpretation of ECG signals is known in the art. Particularly, if the ECG shows elevated ST segments, a ST segment elevated myocardial infarction (STEMI) is diagnosed.

Myocardial infarction (MI), also termed heart attack, is known as cell necrosis in the myocardium resulting from ischemia. Myocardial infarction can be caused by the sudden occlusion or significant narrowing of a coronary artery. The sudden narrowing or occlusion of a coronary artery is frequently caused by the formation of a thrombus after plaque disruption. In case of insufficient collaterals, blood flow is obstructed and the affected myocardium becomes ischemic.

It is well established that the duration of coronary artery occlusion is significant to the nature and extent of myocardial damage. In a first stage after artery occlusion, ischemic damage occurs. This damage may be fully reversible if sufficient blood flow of the occluded artery is reestablished within a short period in time. However, if reperfusion is only achieved within 2 to 4 hours after ischemia, irreversible cardiac injury will develop and postischemic dysfunction may furthermore develop in other parts of the myocardium. Thus early intervention is needed to save myocardium by protecting the affected myocardium from necrosis and to prevent late sequelae of necrosis such as heart failure and to reduce long-term and short-term mortality.

Delayed medical attendance may therefore be an important risk to the health of patients with ST elevation myocardial infarction (STEMI). A substantial patient delay, e.g. defined as the time from symptom onset until first medical contact, can form a leading cause of death in patients with STEMI. In developed countries, median delay time from symptom onset to hospital arrival may range from 1.5 hours to more than 6 hours. Observational studies from data registries indicate that 1 hour reduction in delay may be associated with more than ten extra lives saved per 1000 patients treated. The potential benefits of reducing patient delay may even be underestimated as patients with STEMI dying from ventricular fibrillation in the pre-hospital phase are often not included in registry studies.

Furthermore, the effect of education and public information campaigns on the decision of patients to seek early medical attendance appears rather limited. Therefore, methods for self-diagnosis and early detection of acute coronary artery occlusion (CAO), e.g. a method which allows the subject to perform an initial risk assessment for CAO and/or for establishing a probability of occurrence of a STEMI event, may form an important tool for motivating patients to seek medical assistance in elevated risk situations, and may thus improve the efficiency of medical emergency services, e.g. by reducing the inflow of false positive cases and improving the inflow of patients having an early recognized risk of suffering a STEMI.

Electrocardiograph (ECG) devices for recording bioelectric data from a body are known in the art. For example, in U.S. Pat. No. 6,055,448, a device is disclosed which comprises an array of electrode leads for detecting an electrical signal associated with components of a heartbeat. In a known configuration, such a device can be embodied in an electrode vest comprising, for example, 80 electrode leads. However, for devices and method for self-diagnosis and early detection of acute coronary artery occlusion (CAO), e.g. for performing an initial risk assessment, simple means for recording, e.g. requiring only few electrode leads and simple yet robust means for ECG analysis are preferred.

In U.S. Patent Application No. US 2005/0085736, a portable ECG detector device is disclosed for detecting a myocardial infarction. The device includes a processor which records a baseline ECG from a plurality of electrodes. If data representing current bodily activity deviate from the baseline ECG by a predetermined deviation value, the user is notified to seek medical attention. The baseline ECG reference data thereby typically is recorded for a user lying down in a supine position having his legs raised. While this prior art device allows detection of elevation or depression of the ST-segment above or below a predetermined level in relation to the baseline ST-segment recording, there is still room for improved sensitivity and specificity for raising an attention signal, for example, to avoid that normal physiological variations are mistaken for a ST-segment deviation indicative of a health risk.

SUMMARY OF THE INVENTION

It is an object of embodiments of the present invention to provide means and methods for fast and efficient preliminary analysis of the ST-segment in an electrocardiogram.

The above objective is accomplished by a method and device according to the present invention.

The present invention relates to a device for analyzing electrocardiogram data, the device comprising an input means for obtaining a temporal sequence of electrocardiogram data registered by a plurality of electrodes corresponding to a plurality of predetermined locations on the body of a user, a processing unit connected to said input means to receive and process the temporal sequence of electrocardiogram data, the processing unit being programmed for determining at least one parameter indicative of a morphological feature from said temporal sequence of electrocardiogram data and for performing a comparison of said at least one parameter to a previously recorded distribution of said at least one parameter obtained from said user under a plurality of different physiological conditions and optionally stored on a memory of the device, and an output means connected to said processing unit for generating a signal taking into account said comparison, the signal being representative of a risk of a myocardial infarction occurring in said body. The morphological feature comprises a multi-dimensional ST segment feature, e.g. an ST-vector.

The electrocardiogram data registered by at least 2 electrodes corresponding to a plurality of predetermined locations on the body of a user may comprise a first bipolar measurement obtained between a chest electrode point on the body located between 3 cm and 6 cm above the fourth left parasternal intercostal space and a location on the right upper extremity.

The electrocardiogram data registered by at least 2 electrodes corresponding to a plurality of predetermined locations on the body of a user furthermore may comprise a second bipolar measurement obtained between the left crista iliaca and the location on the right upper extremity, and a third bipolar measurement obtained between a location on the left upper extremity and the location on the right upper extremity.

The electrocardiogram data may comprise a) a first bipolar measurement obtained between a chest electrode point on the body located between 3 cm and 6 cm above the fourth left parasternal intercostal space and a location on the right upper extremity, b) a second bipolar measurement obtained between the left crista iliaca and the location on the right upper extremity, and c) a third bipolar measurement obtained between a location on the left upper extremity and the location on the right upper extremity.

It is an advantage of embodiments according to the present invention that a notification signal can be raised with good specificity and sensitivity for indicating a risk of myocardial infarction, indicative for a probable occurrence of an acute coronary artery occlusion event.

In a device according to embodiments of the present invention, the processing unit may be adapted for performing the comparison by comparing the at least one parameter to a previously recorded individual spatial reference of the at least one parameter obtained from the user under a plurality of different physiological conditions.

It is an advantage of embodiments according to the present invention that an analysis may be performed which is personalized to the physiological characteristics of the subject being monitored. It is an advantage of embodiments according to the present invention that a self-assessment can be performed by a user, e.g. without requiring intervention of medically qualified personnel, for early detection of acute coronary artery occlusion (CAO), e.g. for an initial risk assessment for CAO.

The different physiological conditions may be more than three different physiological conditions, e.g. more than six different physiological conditions, e.g. more than ten different physiological conditions.

The device may furthermore be adapted for prompting the user for inputting during a calibration and/or re-calibration procedure a temporal sequence of electrocardiogram data registered by a plurality of electrodes corresponding to the plurality of predetermined locations on the body of the user obtained under a plurality of different physiological conditions. It is an advantage of embodiments of the present invention that a user friendly device is obtained that allows a self-assessment that can be performed with low sensitivity to false positives due to physiological variations.

The processing unit may furthermore be adapted for deriving an updated distribution of said at least one parameter based on said temporal sequences inputted during a re-calibration procedure. It is an advantage of embodiments according to the present invention that a self-assessment can be performed with low sensitivity to false positives due to physiological variations, e.g. due to physical exertion. It is an advantage of embodiments according to the present invention that a self-assessment can be performed with low sensitivity to slow shifts in physiological parameters over time.

The device furthermore may be adapted for storing the updated distribution in a memory means and using the updated distribution in the comparison in future measurements.

In a device according to embodiments of the present invention, the processing unit may be adapted for performing the comparison of the at least one parameter to the previously determined distribution by subtracting, from the at least one parameter, an average of the at least one parameter obtained from the user under a plurality of different physiological conditions, corresponding to the previously recorded individual spatial reference, such as to obtain a shift vector. The processing unit may be further adapted for applying a coordinate transformation to this shift vector.

In a device according to embodiments of the present invention, the processing unit may be adapted for applying the coordinate transformation to the shift vector, in which the coordinate transformation is determined by a principal component analysis of a further distribution of the at least one parameter over a population of reference samples obtained from a plurality of different individuals.

In a device according to embodiments of the present invention, the processing unit may be adapted for applying the coordinate transformation to the shift vector, in which the coordinate transformation is determined by a principal component analysis of the at least one parameter obtained from the user under a plurality of different physiological conditions corresponding to the previously recorded individual spatial reference. The input means may comprise the plurality of electrodes. It is an advantage of embodiments of the present invention that a device can be provided that allows both measurements, processing and indicating results.

The plurality of electrodes may consist of two electrodes. It is an advantage of embodiments of the present invention that a device can be provided that easily allows measurements by a user.

The device may be adapted in volume and mass to be transportable in a clothing pocket or handbag. It is an advantage of embodiments of the present invention that a user friendly device is provided.

The device may be integrated into a mobile phone or a tablet computer. It is an advantage of embodiments of the present invention that the device can be combined with widely spread consumer devices, such as a mobile phone, e.g. a smartphone, or a tablet computer.

The device may be adapted for, for generating the signal, taking into account a further distribution of said at least one parameter, in which said further distribution is obtained from a population of reference individuals. It is an advantage of embodiments of the present invention that the techniques can be easily combined with other existing techniques for further improving detectivity.

The device may be adapted for prompting a user with a self-evaluation questionnaire and for taking into account, for generating the signal, answers to a self-evaluation questionnaire. It is an advantage of embodiments of the present invention that the techniques can be easily combined with other existing techniques for further improving specificity.

The present invention also relates to a method for analyzing electrocardiogram data, the method comprising obtaining a temporal sequence of electrocardiogram data registered by at least two electrodes corresponding to a plurality of predetermined locations on the body of a user, determining at least one parameter indicative of a morphological feature from said temporal sequence of electrocardiogram data; obtaining a previously recorded individual spatial reference of said at least one parameter obtained from said user under at least two different physiological conditions; performing a comparison of said at least one parameter to said previously recorded individual spatial reference of said at least one parameter; and generating a signal taking into account said comparison. The morphological feature comprises a multi-dimensional ST segment feature, e.g. an ST-vector.

In a method according to embodiments of the present invention, performing the comparison may comprise subtracting from the at least one parameter an average of the at least one parameter obtained from the user under the at least two different physiological conditions, e.g. corresponding to the previously recorded individual spatial reference of the at least one parameter, Obtaining a temporal sequence of electrocardiogram data may comprise obtaining at least three time series of bipolar measurements, each of the time series being recorded consecutively.

A method according to embodiments of the present invention, may further comprise a step of obtaining a previously recorded individual spatial reference of the at least one parameter obtained from the user under at least two different physiological conditions, and in which the previously determined distribution of the at least one parameter comprises the previously recorded individual spatial reference of the at least one parameter. The predetermined positions may be at least one reference location on the right side of the thorax and at least two, preferably at least three locations on the left side of the thorax.

The at least two different physiological conditions may be representative for most or all physiological conditions wherein measurements may be taken in the future. The method may comprise, prior to said obtaining, updating the distribution of said at least one parameter obtained from said user under a plurality of different physiological conditions. Updating may comprise obtaining a temporal sequence of electrocardiogram data registered by a plurality of electrodes corresponding to the plurality of predetermined locations on the body of the user under a plurality of different physiological conditions, as prompted.

Obtaining the temporal sequence of electrocardiogram data may comprise obtaining the temporal sequence of electrocardiogram data, in which the electrocardiogram data comprises a first bipolar measurement between a chest electrode point (VE) and the right shoulder (VR), a second bipolar measurement between the left crista iliaca (VF) and the right shoulder (VR), and a third bipolar measurement between the left shoulder (VL) and right shoulder (VR).

Performing said comparison may comprise subtracting from the at least one parameter an average of said at least one parameter obtained from said user under said at least two different physiological conditions, corresponding to said previously recorded individual spatial reference of said at least one parameter, to obtain a shift vector, and applying a coordinate transformation to said shift vector.

Applying said coordinate transformation to said shift vector may comprise determining said coordinate transformation by a principal component analysis of a further distribution of the at least one parameter over a population of reference samples obtained from a plurality of different individuals.

Applying said coordinate transformation to said shift vector may comprise determining said coordinate transformation by a principal component analysis of said at least one parameter obtained from said user under a plurality of different physiological conditions corresponding to said previously recorded individual spatial reference.

Obtaining the temporal sequence of electrocardiogram data may comprise obtaining electrocardiogram data using a measurement wherein the chest electrode point is located between 3 cm and 6 cm above the fourth left parasternal intercostal space on the body.

Generating said signal may comprise generating said signal representative of a risk of an acute coronary artery occlusion by acute regional transmural ischemia detection.

Determining the at least one parameter may comprise determining at least one value indicative of a morphological feature from the temporal sequence of electrocardiogram data.

Determining the at least one parameter may comprise determining at least one value indicative of a morphological feature defined for a local time interval less than the duration of a representative heartbeat.

Determining the at least one parameter may comprise determining at least one value indicative of a property of at least one ST segment in said temporal sequence of electrocardiogram data.

Determining at least one parameter may comprise determining at least one value indicative of J-point elevation.

Determining at least one parameter may comprise, for each subsequence corresponding to a single heartbeat in said temporal sequence, detecting a first fiducial marker in the ST segment and detecting a second fiducial marker in the PR segment, and calculating the difference in amplitude between the first fiducial marker and the second fiducial marker aggregated over a plurality of said subsequences.

The method furthermore may comprise preprocessing said temporal sequence of electrocardiogram data for reducing noise and uninformative contributions to said electrocardiogram data.

Generating the signal representative of the risk of a myocardial infarction occurring in said body furthermore may take a further distribution of said at least one parameter into account, in which said further distribution is obtained from a population of reference individuals.

Generating the signal representative of the risk of a myocardial infarction may comprise taking answers provided by said user in response to a self-evaluation questionnaire into account.

The present invention also relates to an application program product for, when executing on a computing device, executing a method as described above.

The present invention also relates to a computer-readable data carrier storing an application program product as described above.

The present invention also relates to the transmission of an application program product as described above over a communication network.

The present invention furthermore relates to the use of a device as described above or of an application program product as described above for self-assessment of a cardiovascular health risk.

The plurality of different physiological conditions as used in the method and/or device according to embodiments of the present invention may be chosen to be representative for the situations in which a myocardial infarction could take place, i.e. for instance physiological conditions that a user frequently performs.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
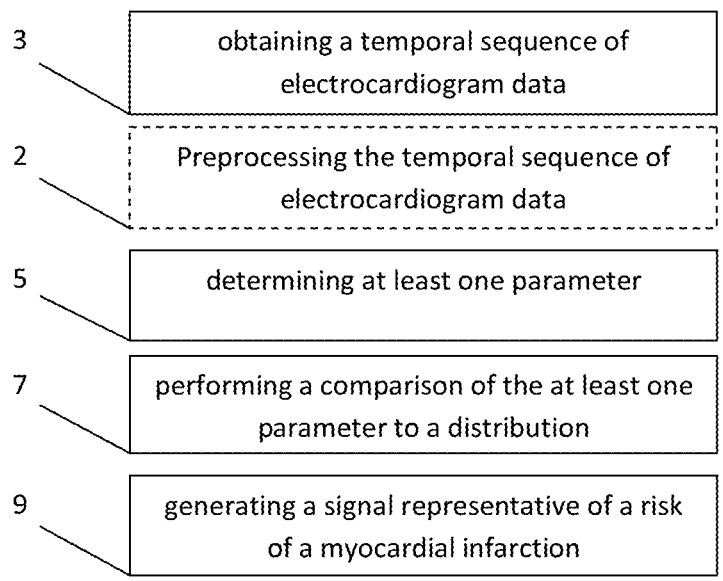
FIG. 1 shows an exemplary method according to embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to a method for analyzing electrocardiogram data. This method comprises obtaining a temporal sequence of electrocardiogram data registered by a plurality of electrodes corresponding to a plurality of predetermined locations on the body of a user. The method further comprises determining at least one parameter indicative of a morphological feature from the temporal sequence of electrocardiogram data, and performing a comparison of the at least one parameter to a previously determined distribution of the at least one parameter obtained from the user under a plurality of different physiological conditions, e.g. a plurality of predetermined physiological conditions. The morphological feature comprises a multi-dimensional ST segment feature, for example a vector ST segment feature, such as an ST-injury vector. The method also comprises generating a signal taking into account this comparison, for example a signal representative of a risk of a myocardial infarction occurring in the body of the user.

Obtaining the temporal sequence of electrocardiogram data may comprise obtaining a temporal sequence of electrocardiogram data, in which the electrocardiogram data comprises a first bipolar measurement between a chest electrode point on the body located between 3 cm and 6 cm above the fourth left parasternal intercostal space and a location on the right upper extremity, e.g. the right shoulder, a second bipolar measurement between the left crista iliaca and the location on the right upper extremity, e.g. the right shoulder, and a third bipolar measurement between a location on the left upper extremity, e.g. the left shoulder, and the location on the right upper extremity, e.g. the right shoulder.

In a method according to embodiments of the present invention, performing the comparison may comprise subtracting from the at least one parameter an average of this at least one parameter obtained from the user under the at least two different physiological conditions, e.g. corresponding to the previously recorded individual spatial reference of said at least one parameter, to obtain a shift vector, and applying a coordinate transformation to this shift vector. By way of illustration standard and optional features will further be described with reference to the drawings, embodiments of the present invention not being limited thereto.

Referring to FIG. 1, an exemplary method 1 for analyzing electrocardiogram data according to embodiments of the present invention is shown. The method 1 may according to embodiments of the invention, be entirely or in part a computer-implemented method, for example the method 1 or steps of the method 1 may be implemented in software for execution on a handheld computing device, such as, for example, a mobile phone. In particular embodiments, the method may be implemented as application program product, also referred to as applet.

This method 1 comprises in a first step obtaining 3 a temporal sequence of electrocardiogram data registered by a plurality of electrodes corresponding to a plurality of predetermined locations on the body of a user. It thereby is to be noticed that when using a handheld device, the plurality of electrodes may be two electrodes, the two electrodes being sufficient for recording the required data. When applying wired electrodes, typically one uses at least 4 electrodes for obtaining 3 bipolar measurements.

Figure 4:
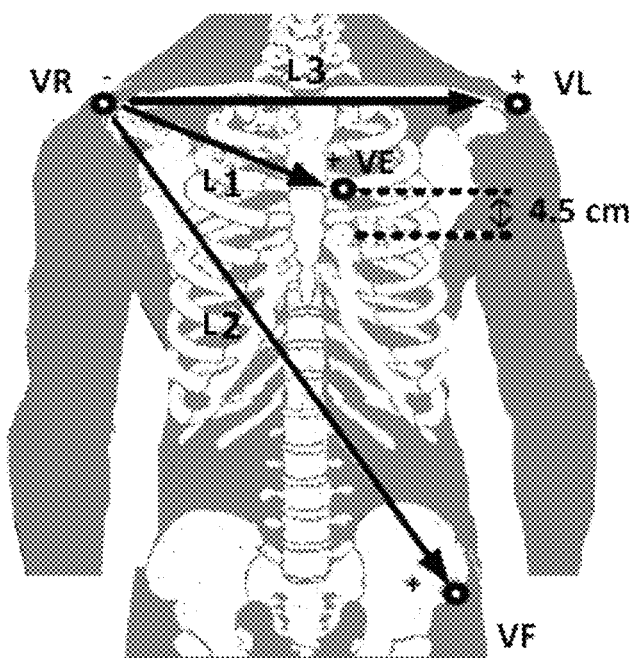
FIG. 4 shows an exemplary electrode lead positioning system for use with a method according to embodiments of the present invention.

In particular embodiments of the present invention, obtaining 3 this temporal sequence of electrocardiogram data may comprise obtaining 3 a temporal sequence of electrocardiogram data, in which the electrocardiogram data comprises a first bipolar measurement between a chest electrode point VE on the body located between 3 cm and 6 cm above the fourth left parasternal intercostal space and a location on the right upper extremity, e.g. the right shoulder VR, a second bipolar measurement between the left crista iliaca VF and the location on the right upper extremity, e.g. the right shoulder VR, and a third bipolar measurement between a location on the left upper extremity, e.g. the left shoulder VL, and the location on the right upper extremity, e.g. the right shoulder VR. Such a configuration may result in little variation during physiological conditions with high sensitivity for pathological conditions and is user friendly, as the measurements may be in a significant number of cases be performed without the need for removing clothes. The corresponding lead configuration used in the present example is shown in FIG. 4. It is to be noted that although the electrocardiogram data may comprise additional data corresponding to further electrode lead configurations, e.g. obtained by electrodes located at other points on the body, the electrocardiogram data may consist of the first, second and third bipolar measurement in advantageous embodiments of the present invention. The electrocardiogram data may comprise at least two, advantageous at least 3 different bipolar measurements. A bipolar measurement is a measurement of a potential difference between two predetermined locations, at least one of the predetermined locations being a location on the body of a user. The reference for the measurement may be outside the human body. With different bipolar measurements is meant bipolar measurements wherein the location of at least one of the electrodes on the human body differs for different bipolar measurements. The temporal sequence of electrocardiogram data may comprise at least one time series for each of the bipolar measurements. The temporal sequence of this electrocardiogram data thus may consist of at least one time series of the first bipolar measurement, at least one time series of the second bipolar measurement and at least one time series of the third bipolar measurement. These time series may comprise first, second and third bipolar measurements corresponding to substantially the same points in time, e.g. may be obtained simultaneously, but may also be obtained consecutively, e.g. by positioning a pair of electrodes on the corresponding reference points on the body for each bipolar measurement in a sequence or with a handheld device comprising at least two electrodes and positioning the handheld device consecutively on different locations of the human body.

In the configuration described above, left shoulder and right shoulder may refer to standard ECG electrode positioning locations on the body of the user, e.g. the top of the left shoulder and the top of the right shoulder respectively, as for example the Lund configuration as described and validated (Trägårdh-Johansson E et. al., Journal of Electrocardiology, 44(2011) 109-114). However, one or more of these points may also refer to another location on respectively the left and right upper extremity, e.g. the left and right wrist or hand. Furthermore, the chest electrode point may preferably be located between 3.5 and 5.5 cm above the fourth left parasternal intercostal space, e.g. even more preferred, at substantially 4.5 cm above the fourth left parasternal intercostals space. The chest electrode point may be 4.5 cm above the conventional V2 point.

It is an advantage of this bipolar lead configuration that only three leads are necessary to obtain good results, that the electrode positioning is easy and reproducible, that the obtained electrocardiogram data is sensitive to ST changes during occlusion in each of the three coronary territories, and that the obtained electrocardiogram data is less sensitive to ST variations in physiological conditions.

Figure 5:
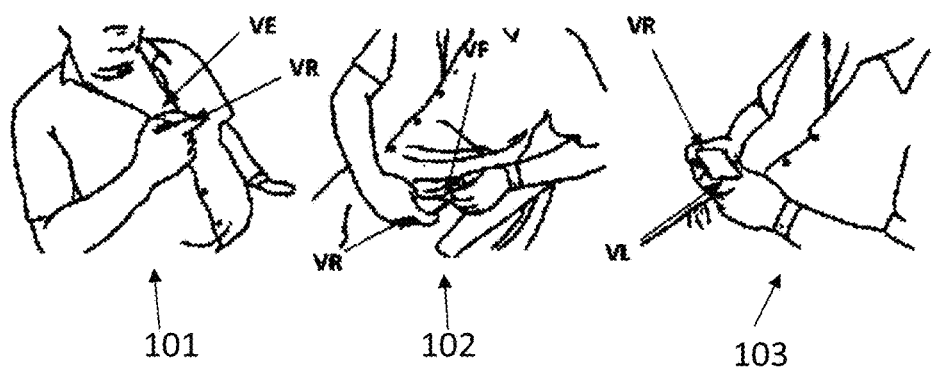
FIG. 5 shows a procedure for self-application of a simple single bipolar measurement device for acquiring electrocardiogram data for the electrode lead positioning system shown in FIG. 4, in accordance with embodiments of the present invention.

It is a further advantage of the described 3-lead ECG configuration that data may be easily obtained by the user, for example, by collecting data time series consecutively for the three bipolar measurements. Referring to FIG. 5, an example is shown how such data collection may be possible through a small, handheld device, e.g. a mobile phone with an integrated ECG electrode. First, in step 101, ECG data is sampled corresponding to the first bipolar measurement, measuring an electrical potential difference over the points VE and VR, then, in step 102, ECG data is sampled corresponding to the second bipolar measurement, measuring an electrical potential difference over the points VR and VF, and finally, in step 103, ECG data is sampled corresponding to the third bipolar measurement, measuring an electrical potential difference over the points VL and VR. It may be noted that, the reference electrode which participates in all three steps, e.g. the VR point, may correspond to a reference potential on the hand in which the device used for these measurements is held, e.g. such that the steps 101, 102 and 103 may be easily executed by bringing a surface electrode on the device into contact with the corresponding other voltage point on the body.

Figure 6:
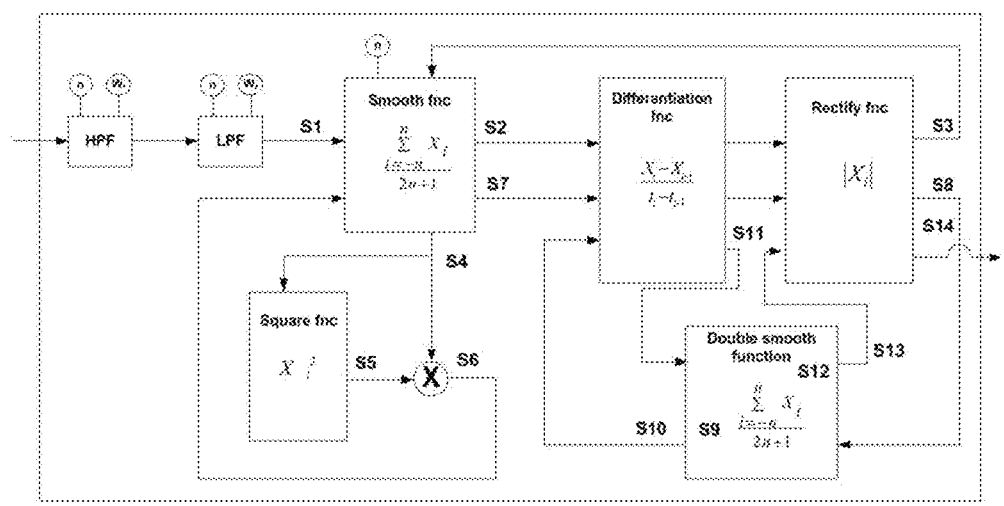
FIG. 6 shows a block diagram for an exemplary preprocessing of electrocardiogram data in a method according to embodiments of the present invention.

The method 1 according to embodiments of the present invention may also comprise a preprocessing 2 of the temporal sequence of electrocardiogram data, e.g. for reducing noise and uninformative contributions to the electrocardiogram data. An exemplary block diagram of such a preprocessing 2 is shown in FIG. 6. Such preprocessing 2 may comprise correcting S1 of baseline wandering by using a high-pass filter HPF and removing muscle interference by applying a low-pass filter HLF. The preprocessing 2 may further comprise smoothing S2, e.g. by using a moving average filter, and determining S3 the slope between consecutive data points (dv/dt) for then rectifying the signal.

The preprocessing 2 may comprise smoothing S4 by using a moving average filter, amplifying S5 the signal, e.g. by applying a square function, and multiplication S6 of the amplified signal with the smoothed signal from S4.

The preprocessing 2 may further comprise again smoothing S7 by using a moving average filter, determining S8 the slope between consecutive data points (dv/dt) and rectifying the signal, two-steps smoothing S9, S10 of the signal by using a moving average filter, determining S11 the slope between consecutive data points, two-steps S12,S13 smoothing of the signal by using a moving average filter and finally S14 rectifying the signal.

However, the preprocessing 2 described hereinabove in relation to FIG. 6 is only exemplary, and any combination of known preprocessing techniques for ECG data may be suitable, as will be clear to the person skilled in the art.

The method 1 comprises in a following step the determining 5 of at least one parameter indicative of a morphological feature from the temporal sequence of electrocardiogram data.

Determining 5 the at least one parameter may comprise determining at least one value indicative of a morphological feature of the temporal sequence of electrocardiogram data. This morphological feature comprises a multi-dimensional ST segment feature, such as an ST-injury vector.

Determining 5 the at least one parameter may comprise determining at least one value indicative of a morphological feature defined for a local time interval less than the duration of a representative heartbeat.

Determining 5 the at least one parameter may comprise determining at least one value indicative of a local feature of the temporal sequence of electrocardiogram data, e.g. determining at least one value which includes a measure of a morphological feature defined for a local time interval less than the duration of a representative heartbeat. For example, such local morphological feature may comprise a measure of J-point elevation.

Determining 5 the at least one parameter may comprise determining at least one value indicative of a property of at least one ST segment in the temporal sequence of electrocardiogram data.

For example, the at least one parameter may comprise a multi-dimensional ST segment feature, e.g. a three-dimensional vector of ST segment features.

Figure 2:
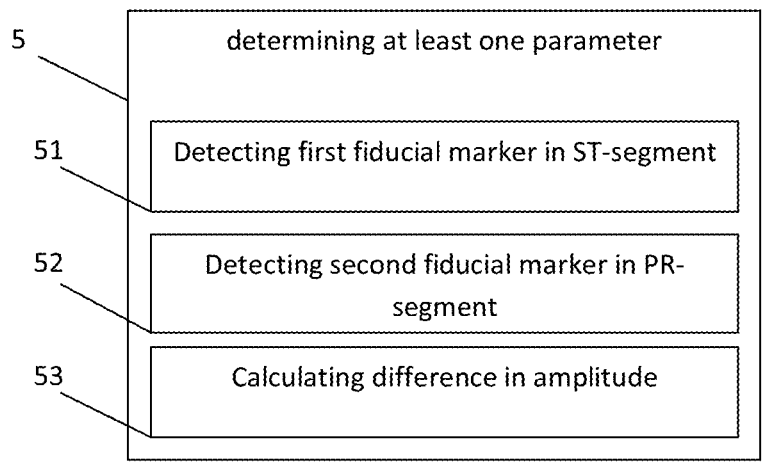
FIG. 2 shows an exemplary method for determining the at least one parameter in a method according to embodiments of the present invention.

As shown in FIG. 2, determining 5 at least one parameter may comprise, in particular embodiments of the present invention, for each subsequence corresponding to a single heartbeat in the temporal sequence, detecting 51 a first fiducial marker in the ST segment and detecting 52 a second fiducial marker in the PR segment, and calculating 53 the difference in amplitude between the first fiducial marker and the second fiducial marker aggregated over a plurality of these subsequences. The at least one parameter may for example comprise multiple scalar values corresponding to such calculated 53 differences in amplitude obtained for different electrocardiogram electrodes, e.g. the at least one parameter may comprise a vector comprising three components, each component being a difference in amplitude, e.g. calculated 53 as explained hereabove, corresponding to a different electrode lead component in the temporal sequence of electrocardiogram data.

Figure 7:
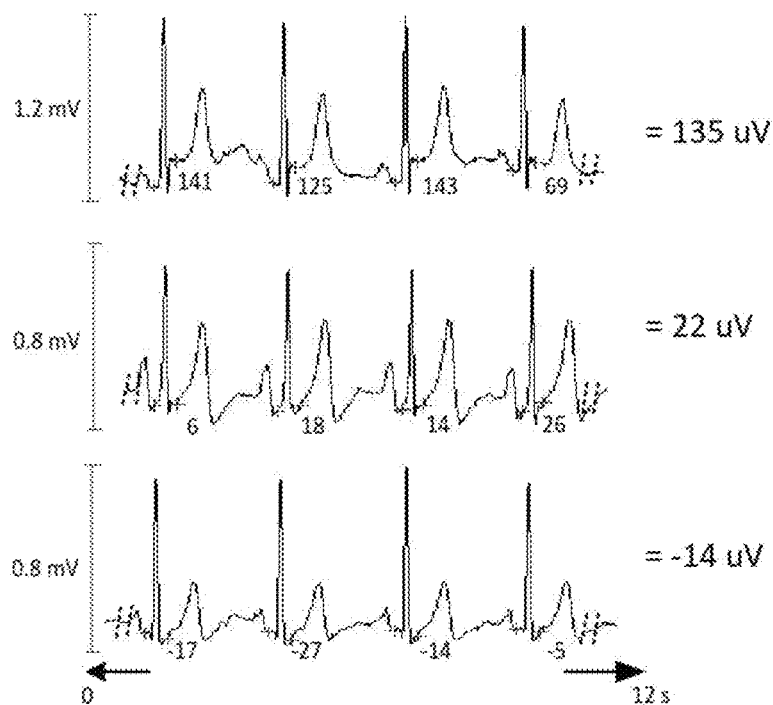
FIG. 7 shows an exemplary data plot corresponding to a baseline measurement in a healthy user over 12 s using the 3-lead system described above in relation to FIG. 4, in accordance with embodiments of the present invention.

For example, determining 5 the at least one parameter according to this exemplary embodiments is illustrated by the exemplary data plot in FIG. 7, which shows a baseline measurement, e.g. in a healthy individual in rest, over 12 s using the 3-lead system described above in relation to FIG. 4. For each of the three ECG measurement components, the first and second fiducial markers are determined, indicated by cross marks. The median value of the differences in amplitude between these markers, over all heart beats within the 12 s window, renders a vector component of the three-dimensional vector (135 µV, 22 µV, −14 µV) which forms, in this example, the at least one parameter. For comparison, when applied to a second exemplary data set shown in FIG. 8, corresponding to the same lead system collected over 12 s but under coronary artery obstruction conditions, determining 5 the at least one parameter in the same way would result in the vector (561 µV, 19 µV, 44 µV).

In a further step, the method 1 comprises performing 7 a comparison of the at least one parameter to a previously determined distribution of the at least one parameter.

The at least one parameter may for example comprise a three-dimensional feature vector derived from ST data. The previously determined distribution of such at least one parameter may for example be encoded by a concatenated list of such vectors, e.g. to form a reference library of vectors. However, the reference vectors, e.g. of the representative ST data, may also be mathematically projected onto predetermined basis vectors for defining signal subspaces of ST data exhibiting normal physiological conditions within the sample population and of ST data exhibiting behavior that can occasion a warning signal to be generated 9. Particularly, a basis transformation may be executed to linearly separate a first subspace corresponding to normal physiological conditions from a second subspace corresponding to alert conditions. Thus performing 7 a comparison of the at least one parameter to a previously determined distribution of the at least one parameter may comprise applying a basis transformation to the at least one parameter, in which this basis transformation is determined by taking the previously determined distribution into account. This transformation may comprise an origin shift, e.g. by subtracting an average of the at least one parameter obtained for the previously determined distribution from the at least one parameter obtained for the user, and/or a rotation and/or a scaling and/or a skewing operation, e.g. an affine coordinate transformation. The projection coefficients, e.g. the at least one parameter being transformed by said transformation, may be further evaluated, for example by a classifier, to determine whether these projection vectors are indicative of a health warning condition, e.g. an ARTI.

A method according to embodiments of the present invention may comprise a step of obtaining a previously recorded individual spatial reference of the at least one parameter obtained from the user under at least two different physiological conditions. In such embodiments, the previously determined distribution of the at least one parameter may comprise the previously recorded individual spatial reference of the at least one parameter. The previously determined distribution is obtained from the user under a plurality of physiological conditions, i.e. previously recorded under a plurality of physiological conditions. For example, a handheld device for at least partially implementing the method 1 may store a personalized library of data during standardized physiological conditions. In particularly advantageous embodiments of the present invention, the distribution of the at least one parameter obtained from the user under a plurality of physiological conditions may be obtained by the user, e.g. without requiring intervention of technically or medically qualified personnel, and without requiring additional equipment, e.g. only using a device for implementing the method 1. Furthermore, the distribution of the at least one parameter may be stored on such device and updated occasionally, e.g. replaced by a new such distribution or extended by new data gathered on this distribution, such that the model for this at least one parameter encoded by the distribution can follow slow changes in time which represent slow physiological changes unrelated to the coronary artery occlusion indication function provided by the method 1.

This personalized library may thus be loaded by self-measurements performed by the user with a handheld device during standardized physical conditions, for example under diverse conditions of metabolic exertion, e.g. in rest, during or subsequent to a slow walk, and/or after jogging, or e.g. in supine position while resting, while standing up in rest, and again after performing a set of genuflexions. Consequently, the library may contain a range of data that are representative of the user's physiological variations under normal conditions, e.g. when no indications exist for raising a health warning for coronary artery occlusion.

According to some embodiments of the present invention, the method thus may comprise, prior to obtaining the results, updating the distribution of the at least one parameter obtained from the user under a plurality of different physiological conditions. Such updating may comprise obtaining a temporal sequence of electrocardiogram data registered by a plurality of electrodes corresponding to a plurality of predetermined locations on the body of a user under a plurality of different conditions, as prompted.

The comparison of the at least one parameter to the distribution thus may allow the acquired ECG data, for example obtained during a symptomatic event, e.g. when the user performs the method 1 in response to experiencing chest pain symptoms, to be compared to the users' physiological library encoding the distribution of the at least one parameter within the same subject, i.e. the user, under a range of different, yet normal, physiological conditions.

The at least one parameter may for example comprise a three-dimensional feature vector derived from ST data. The distribution of such at least one parameter over standardized physiological conditions may for example be encoded by a concatenated list of such vectors over the different physiological conditions, e.g. to form a reference library of vectors. However, the reference vectors, e.g. of the representative ST data, may also be mathematically projected onto predetermined basis vectors for defining signal subspaces of ST data exhibiting normal physiological conditions personalized to the user and of ST data exhibiting behavior that can occasion a warning signal to be generated 9. Particularly, a basis transformation may be executed to linearly separate a first subspace corresponding to normal physiological conditions from a second subspace corresponding to alert conditions.

The comparison 7 of the at least one parameter to a distribution of the at least one parameter obtained from the user under a plurality of physiological conditions may thus comprise applying a basis transformation, determined in part or entirely by the distribution of the at least one parameter obtained from the user under a plurality of physiological conditions, to the at least one parameter in order to obtain projection coefficients, forming e.g. three-dimensional features, which may be further evaluated, e.g. by a classifier, to determine whether these projection vectors are indicative of a health warning condition, e.g. an ARTI.

According to an embodiment of the present invention, the ARTI detection process furthermore may compare both personal data, such as age, gender, etc. and the three-dimensional features obtained during a symptomatic event with those from the users library of physiological variations. The personal data and three-dimensional features may be either separately evaluated with the results combined, or evaluated in combination to produce a single result, yielding a final decision of whether an acute coronary occlusion is present in the patient."

Figure 8:
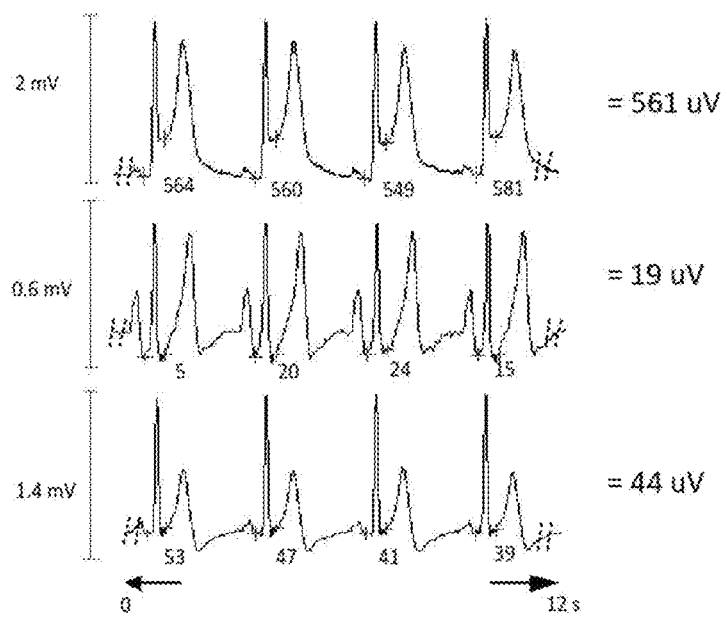
FIG. 8 shows a second exemplary data plot corresponding to a measurement under coronary artery obstruction conditions over 12 s using the 3-lead system described above in relation to FIG. 4, in accordance with embodiments of the present invention.
Figure 9:
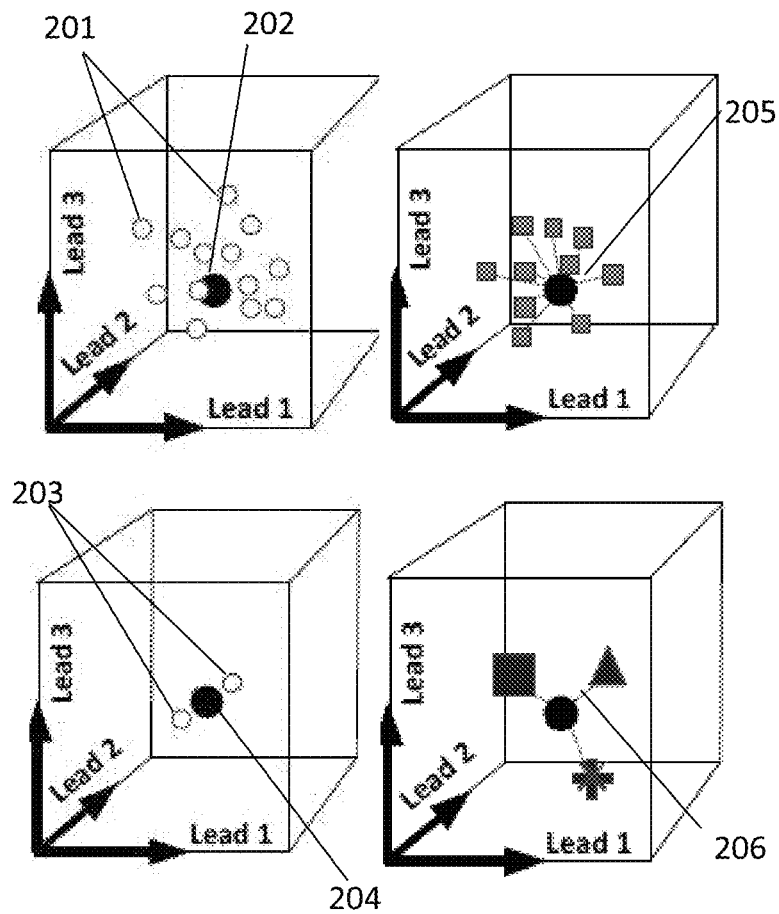
FIG. 9 shows exemplary data for illustrating the comparison of the at least one parameter to the distribution in accordance with embodiments of the present invention.

For example, the comparison 7 of the at least one parameter to the distribution of the at least one parameter obtained from the user under a plurality of physiological conditions is illustrated in FIG. 9 by exemplary data. Here, the at least one parameter comprises three scalar components of a vector as illustrated in FIG. 7 and FIG. 8 and described hereinabove. The at least one parameter may be obtained from the user under a plurality of physiological conditions, e.g. represented by the plurality of plot points 201,203. The data thus obtained may be used for charactering the distribution thereof, e.g. a mean value 202,204 for the at least one parameter under the plurality of physiological conditions may be stored for characterizing the distribution in a user-specific, e.g. a personalized, manner. While in simple embodiments the distribution may be characterized by merely storing the list of values for the at least one parameter under the plurality of physiological conditions, or by merely storing the component-wise average thereof, in other embodiments, the distribution may be characterized by, for example, a mean and standard deviation per component, a median and first and third quartile value per component, a component-wise average and covariance matrix, or may even include higher order moments such as skewness or curtosis.

The at least one parameter determined 5 in a previous step of the method 1 may thus be compared to this reference distribution, e.g. by subtracting the stored mean value 202, 204 such that a shift vector 205,206 is obtained. In other embodiments, a mean and standard deviation or mean and covariance matrix characterizing the distribution may be used to determine a normal standardized value, e.g. a z-score. However, surprisingly, even the easily computable shift vector 205, 206 can be sufficient to compensate for physiological variation of the at least one parameter in a subject.

Figure 10:
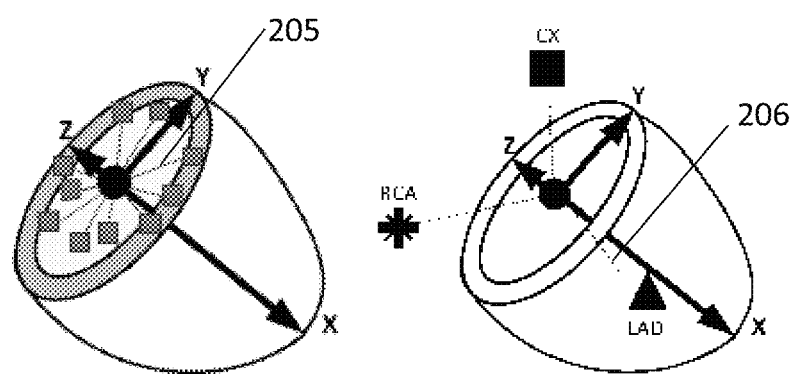
FIG. 10 shows an exemplary basis transformation applied to the exemplary data in FIG. 9 in order to separate conditions for generating a signal from uneventful conditions, in accordance with embodiments of the present invention.

The comparison 7 may further comprise a suitable basis transformation in order to linearly separate normal physiological responses from conditions which should generate 9 a warning signal. FIG. 10 shows such an exemplary basis transformation applied to the exemplary data in FIG. 9. Here the shift vectors 205 obtained from a user under normal physiological conditions is shown to lie within a well-defined region of the vector space. On the other hand, the shift vectors 206 obtained under warning conditions, e.g. under coronary artery occlusion conditions, are clearly well-separated from this well-defined region of vector space.

In a yet further step, the method 1 comprises generating 9 a signal taking into account the comparison, in which this signal is representative of a risk of a myocardial infarction occurring in the body. In embodiments according to the present invention, the signal may be representative of a risk of an acute coronary artery occlusion, e.g. the signal may be generated by acute regional transmural ischemia detection taking into account the comparison of the at least one parameter to the predetermined distribution.

In a method 1 according to embodiments, generating 9 the signal representative of the risk of a myocardial infarction occurring in the body may take a further distribution of the at least one parameter into account, in which this further distribution characterizes the distribution of the at least one parameter in a population of reference individuals, e.g. in which the further distribution is obtained from a population of reference individuals.

Furthermore, generating 9 the signal representative of the risk of a myocardial infarction may comprise taking answers provided by the user in response to a self-evaluation questionnaire into account, e.g. an automated questionnaire. Additionally, other clinical information, such as the user's age, sex and/or medical history may also be taken into account for generating 9 the signal.

In embodiments of the present invention, the steps of performing 7 the comparison and generating 9 the signal may form distinct operations, e.g. as implemented in a computer program product, or may be integrated in a single operation, for example by the implementation of a binary classifier or a Bayesian or logistic decision function.

In embodiments of the present invention, generating 9 the signal may be performed taking into account a sensitivity/specificity operating point. Such sensitivity/specificity operating point may be selectable, e.g. by adjusting a threshold in a classifier that determines the probability of a myocardial infarction, e.g. the probability of detection of an ARTI condition. According to embodiments of the invention, the sensitivity/specificity operating point may also be adjusted taking into account additional data, for example, the answers to a self-evaluation questionnaire and/or to other clinical information such as referred to hereinabove. For example, when experiencing typical chest pain, a highly sensitive mode may be selected to detect all possible events indicating acute coronary occlusion. If clinical data from the auto questionnaire indicate a low priority probability for coronary artery disease, a highly specific mode may be selected to detect an ARTI. If a potential ARTI is detected in such high specific mode, the user may even record a temporal sequence of ECG data over a longer period or on additional body surface locations in a repeated application of the method to confirm a generated signal.

When a method 1 according to embodiments is implemented in a programmable device, e.g. a handheld device according to the second aspect of the invention, the generated signal may be useful in screening cardiologically risky conditions.

It is to be noted that even though a method according to embodiments of the present invention generates a signal representative of the risk of a myocardial infarction, this is not to be confused with performing a medical diagnosis. In fact, the purpose of such signal may merely reside in providing an additional motivation or constraint, e.g. providing higher selectivity and specificity, to the medically untrained patient before seeking professional medical attention. Therefore, such method is rather intended to be, for example, a burglary alarm based on simple acoustic measurements, e.g. which may be used to motivate the investigation of a suspicious event, as opposed to the act of direct intruder detection by a security guard or law enforcer.

In a second aspect, the present invention relates to a device for analyzing electrocardiogram data. The device comprises an input means for obtaining a temporal sequence of electrocardiogram data registered by a plurality of electrodes corresponding to a plurality of predetermined locations on the body of a user. The device further comprises a processing unit connected to this input means to receive and process the temporal sequence of electrocardiogram data. The processing unit is programmed for determining at least one parameter indicative of a morphological feature from the temporal sequence of electrocardiogram data and for performing a comparison of the at least one parameter to a distribution of the at least one parameter obtained from the user under a plurality of different physiological conditions. The morphological feature comprises a multi-dimensional ST segment feature, e.g. an ST-vector. The device also comprises an output means connected to the processing unit for generating a signal taking into account the comparison. This signal is representative of a risk of a myocardial infarction occurring in said body.

The electrocardiogram data may for example comprise a) a first bipolar measurement obtained between a chest electrode point on the body located between 3 cm and 6 cm above the fourth left parasternal intercostal space and a location on the right upper extremity, b) a second bipolar measurement obtained between the left crista iliaca and the location on the right upper extremity, and c) a third bipolar measurement obtained between a location on the left upper extremity and the location on the right upper extremity. For example, the processing unit, or the processing unit and the input means, may be specifically configured to generate said signal when electrocardiogram data comprising the first, second and third bipolar measurement is presented for processing via the input means.

Figure 3:
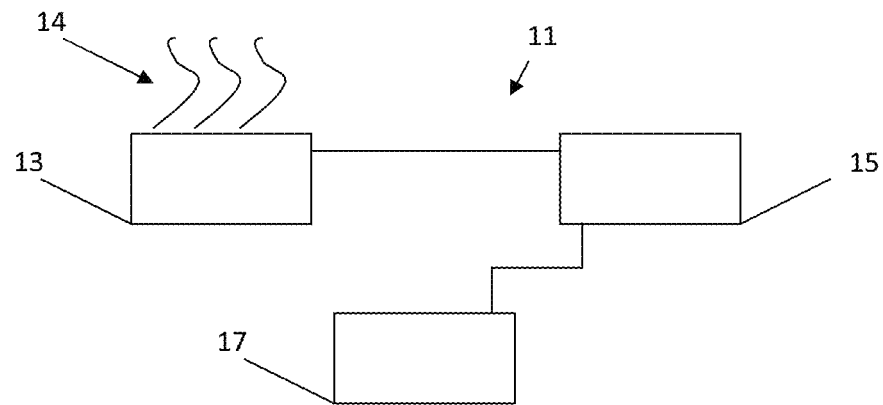
FIG. 3 shows a device according to embodiments of the present invention.

Referring to FIG. 3, a device 11 for analyzing electrocardiogram data is shown according to embodiments of the present invention. The device 11 may be adapted in volume and mass to be transportable in a clothing pocket or handbag, e.g. may weigh less than 1 kg, e.g. preferably less than 500 g, e.g. the device may have a mass in the range of 25 g to 300 g. For example, the device may be integrated into a mobile phone.

The device 11 comprises an input means 13 for obtaining a temporal sequence of electrocardiogram data registered by a plurality of electrodes corresponding to a plurality of predetermined locations on the body of a user. The input means 13 in a device according to embodiments of the invention may also comprise this plurality of electrodes 14. In particular embodiments of the invention, the plurality of electrodes may consist of at least two electrodes, at least three or at least four electrodes. Using at least two electrodes may for instance be used in a handheld device, in which the plurality of different bipolar measurement are registered consecutively by positioning at least one of the two electrodes on different locations on the human body of the user. The plurality of electrodes may alternatively consist of at least three or at least four electrodes. The plurality of electrodes may be integrated in the handheld device or may be add-ons to the device.

The device 11 also comprises a processing unit or processor 15 connected to the input means 13 to receive and process the temporal sequence of electrocardiogram data. This processing unit is programmed for determining at least one parameter indicative of a morphological feature from the temporal sequence of electrocardiogram data and for performing a comparison of the at least one parameter to a distribution of the at least one parameter obtained from the user under a plurality of different physiological conditions.

The device can in one embodiment be adapted for prompting the user for inputting, receiving or recording, during a calibration and/or re-calibration procedure a temporal sequences of electrocardiogram data registered by a plurality of electrodes corresponding to a plurality of predetermined locations on the body of a user obtained under a plurality of different physiological conditions. The processing unit may be adapted for deriving an updated distribution of said at least one parameter based on said temporal sequences inputted during a re-calibration procedure. The device furthermore may be adapted for storing the updated distribution in a memory means and using the updated distribution in the comparison in future measurements.

The processing unit may be adapted for performing the comparison of the at least one parameter to the previously determined distribution by subtracting an average of the at least one parameter obtained from the user under a plurality of different physiological conditions, e.g. corresponding to the previously recorded individual spatial reference, to obtain a shift vector.

The processing unit may further be adapted for applying a coordinate transformation to the shift vector. The processing unit may be adapted for applying the coordinate transformation to the shift vector, wherein this coordinate transformation is determined by a principal component analysis of a further distribution of the at least one parameter over a population of reference samples obtained from a plurality of different individuals. However, the processing unit may also be adapted for, additionally or alternatively, applying the coordinate transformation to the shift vector, wherein the coordinate transformation is determined by a principal component analysis of the at least one parameter obtained from the user under a plurality of different physiological conditions corresponding to the previously recorded individual spatial reference.

According to embodiments of the present invention, the processing unit may be adapted for adapting the comparison of the parameter, depending on a quality of the reference data. For example, in an initial phase, comparison could for example be made to standard reference data that is not stemming from the particular user of the device, e.g. that are previously stored, whereas in a later phase the comparison of the parameter could be performed with respect to a reference that is based on previously stored data of the user. The device 11 also comprises an output means 17 connected to the processing unit 15 for generating a signal taking into account this comparison, in which the signal is representative of a risk of a myocardial infarction occurring in the body of the user.

The device 11 may for example be a mobile phone, e.g. a smartphone, or handheld computing device. Such device may for example comprise at least two electrodes, e.g. two electrodes at opposite surfaces of the device, such that a user may perform sequential measurements by holding the device while contacting one electrode with his right hand and contacting another electrode consecutively to a plurality of anatomical locations, e.g. positions corresponding to the lead positions such as described hereinabove.

A method according to embodiments of the first aspect of present invention may be implemented in a device 11 according to embodiments of the second aspect of the invention, such as the device 11 shown in FIG. 3. The device 11 comprises a processing unit 15 that may, in a particular embodiment, include at least one programmable processor coupled to a memory subsystem that includes at least one form of memory, e.g., RAM, ROM, and so forth. It is to be noted that the processor or processors may be a general purpose, or a special purpose processor, and may be for inclusion in a device, e.g., a chip that has other components that perform other functions. Thus, one or more aspects of the present invention can be implemented in digital electronic circuitry, or in computer hardware, firmware, software, or in combinations of them. The processing system may include a storage subsystem that has at least one storage medium slot, e.g. a memory card reader. In some implementations, a display system, a keyboard, and/or a pointing device may be included as part of a user interface subsystem to provide for a user to manually input information. Ports for inputting and outputting data also may be included. More elements such as network connections, interfaces to various devices, and so forth, may be included, but are not illustrated in FIG. 3. The various elements of the device 11 may be coupled in various ways, including via a bus subsystem, e.g. a system of at least one bus. The memory of the memory subsystem may at some time hold part or all of a set of instructions that when executed on the processing system implement the steps of the method embodiments described herein. Thus, while a processing unit with means for input and for output may be known in the art, a system that includes the instructions to implement aspects of the methods according to embodiments of the first aspect of the invention is not prior art.

In a further aspect, the present invention relates to a computer program product for, when executing on a computing device, executing a method 1 according to the first aspect of the invention. The present invention also relates to a computer-readable data carrier storing a computer program product according to this further aspect, and to the transmission of such computer program product over a communication network.

The present invention thus also includes a computer program product, e.g. an application program product also referred to as applet, which provides the functionality of any of the methods according to the present invention when executed on a computing device. Such computer program product can be tangibly embodied in a carrier medium carrying machine-readable code for execution by a programmable processor. The present invention thus relates to a carrier medium carrying a computer program product that, when executed on computing means, provides instructions for executing any of the methods as described above. The term "carrier medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Common forms of computer readable media include, a CD-ROM, a DVD, a flexible disk or floppy disk, a memory key, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

The present invention also relates to the use of a device according to embodiments of the second aspect of the present invention or of a computer program product such as an applet as described above, for self-assessment of a cardiovascular health risk, e.g. for preliminary assessment of a cardiological risk by a user when, for example, this user experiences chest pain symptoms.

An example for illustrating principles of the present invention will be given further hereinbelow. These examples are intended for illustrating various aspects of the present invention, without being intended to limit the invention in any way to the particular examples set forth.

The present example illustrates a lead positioning method and associated algorithm in accordance with embodiments of the present invention, which may be implemented in a hand held device, such as a mobile phone. An advantageously high sensitivity for ST elevation caused by acute coronary artery occlusion (ACAO) may be achieved by comparing a spatial ST level representation, e.g. a multidimensional vector entity representative of ST level, to previously stored individualized spatial references. To avoid false positives in healthy subjects, the stored references include measurements during different physiological conditions. The lead positioning is easily applicable and the algorithms for detection and decision may operate instantaneously in standalone devices, e.g. may provide fast, near real-time results given the limited processing power of a handheld computing device such as a mobile phone.

In a first example, a study consisting of a group of patients with one minute coronary artery occlusion (CAO) during angioplasty, and a group of healthy subjects was performed. The study was approved by the applicant's institutional ethics committee and written informed consent was obtained from all patients and healthy subjects. Clinical characteristics of the study subjects are summarized in following table of clinical characteristics of the study subjects.

Between September 2010 and October 2012, 56 patients—admitted to the catheterization laboratory at the University Hospital Ghent—for elective percutaneous transluminal coronary angioplasty (PTCA, n=69) were recruited in the first group. Exclusion criteria were ongoing chestpain, ST elevation myocardial infarction <48 hours, or planned angioplasty for a potentially non-viable myocardial segment.

|  | Patients with CAO N = 51 | Healthy subjects N = 30 |
|---|---|---|
| Gender (male) | 30 (59%) | 15 (50%) |
| Age | 69 ± 12.4 | 40 ± 11 |
| LBBB | 0 | 0 |
| RBBB | 5 | 0 |
| Incomplete RBBB | 4 | 2 |
| Atrial fibril | 2 | 0 |
| LAHB | 6 | 0 |
| Ventricular pacing | 1 | 0 |
| Angioplasty | 60 | — |
| LM | 1 | — |
| Lad | 27 | — |
| Rca | 22 | — |
| Cx | 10 | — |

Thirty healthy subjects (mean age 40+/−11.4, range 26-56 years) with no history of coronary artery disease were recruited in the second group. Exclusion criteria were inability to perform genuflexions in standing position, chest deformations preventing standard ECG measurements, and contact allergy for ECG electrodes.

The database was divided equally into a retrospective learning dataset and a prospective validation dataset.

Standard ECG measurements, for comparison and validation, were recorded using the CardioTek EP system (Maastricht, the Netherlands) with 12 leads standard ECG registration (I, II, III, aVR, aVF, aVL and the 6 unipolar precordial leads V1-V6) and four exploratory unipolar leads (E1, E2, E3 and E4). Positioning of the standard limb electrodes was according to the Lund configuration known in the art. Two exploratory electrodes were positioned respectively 4.5 cm above and below the fourth left parasternal intercostal space.

Figure 16:
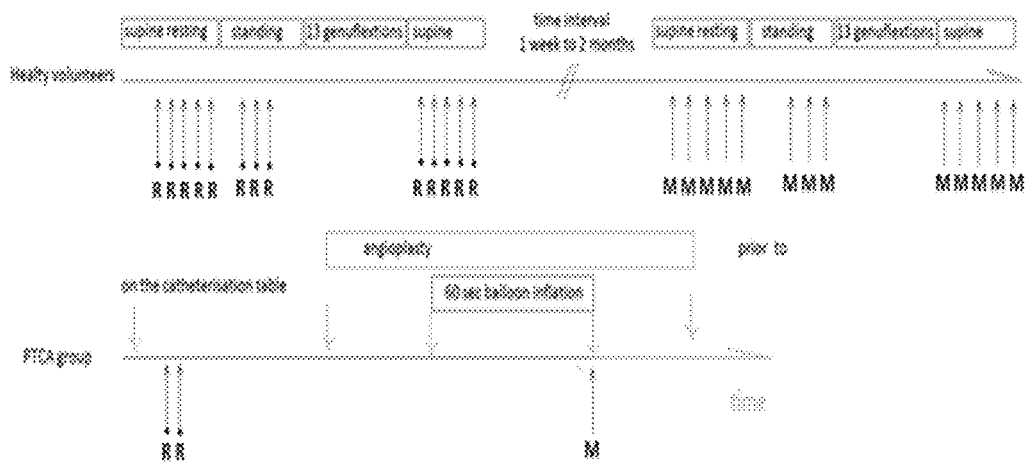
FIG. 16 shows an acquisition timing scheme in an example illustrating embodiments of the present invention.

Duration of each recording was 12 seconds. Sampling rate of the signal was 1000 Hz filtered between 0.05 and 300 Hz. A 50 Hz notch filter was used to suppress mains interferences. Recordings were performed according to the time scheme shown in FIG. 16. Reference measurements R are made under a plurality of conditions, preceding the measurement of interest M.

Figure 15:
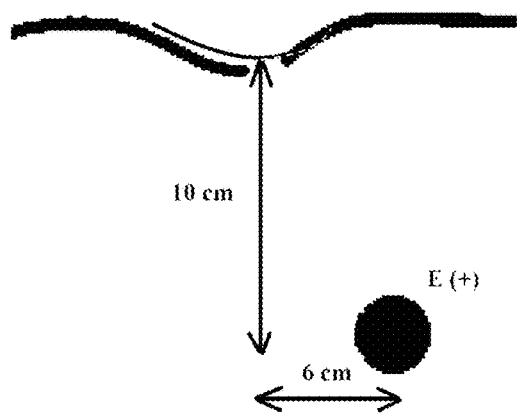
FIG. 15 illustrates a positioning of an electrode 10 cm below the suprasternal notch and 6 cm horizontally left, corresponding to the third intercostal space parasternal left, in accordance with embodiments of the present invention.

A minimal bipolar lead configuration, also shown in FIG. 4, was selected to fulfil the following criteria: 1) easy and reproducible electrode positioning, 2) sensitive for ST changes during occlusion in each of the three coronary territories, and 3) less sensitive to ST variations in physiological conditions. This resulted in a 3-lead configuration system, further referred to as the RELF configuration, consisting of the bipolar measurements between the exploratory electrode VE and the right shoulder (lead L1), the left crista iliaca and the right shoulder (lead L2, equivalent to conventional lead II) and, 3) the left shoulder and right shoulder (lead L3, equivalent to conventional lead I). In all leads, the right shoulder was the negative pole. Lead 1 traces the voltage difference between the right shoulder VR and the exploratory electrode VE, lead 2 between right shoulder and the left shoulder VL and lead 3 between the right shoulder and the left crista iliaca VF. The electrode VE may be positioned positioned 10 cm below the suprasternal notch and 6 cm horizontally left, corresponding to the third intercostal space parasternal left, as illustrated in FIG. 15.

According to embodiments of the present invention, it may be advantageous to use the lead as described above, as it allows obtaining results that can advantageously be used for analysing the occurrence of myocardial infarcts. In a particular aspect, the present invention also relates to a method of using the lead as described above for evaluating occurrence of myocardial infarcts.

An exemplary method according to embodiments of the present invention was implemented in Matlab v7.1 (The MathWorks, Natick, Mass., United States) to detect the level of the ST segment in each of the 3 simultaneously recorded leads (FIG. 4) named respectively ST1, ST2 and ST3. The algorithm consists of 4 main phases. In the first phase, a series of 14 steps was used to process the ECG signal, as shown in FIG. 6. In the second phase, 2 fiducial points (one in the PR segment and one in the ST segment) were determined for each beat within the 12 seconds recording. In the third phase, a set of rules was used to eliminate invalid QRS complexes (extrasystoles and artifacts). In the present example, the set of rules that is used are techniques and algorithms for removing bad QRS complexes from the signal. In the present example, the first and the last QRS complex is removed, since these complexes might not be fully recorded, complexes with very high amplitude compared to the other complexes are removed and high frequency and large amplitude noise waves are removed. In the fourth phase, the median difference in amplitude between the 2 fiducial points was calculated for each valid beat. Finally, the median difference of all beats in the 12 seconds was calculated and denoted as the median ST segment level. These 3 values $a_i$, $b_i$ and $c_i$ form the vector components of an ST-vector in an orthogonal coordinate system (A,B,C). Therefore, the RELF method (RELF lead configuration and ST level algorithm) synthesizes the ST level of a recording into a 3 dimensional point (ai bi ci)

The ST segment amplitudes in the 3 leads thus define the 3D coordinates for spatial ST segment positioning. It was hypothesized that 1) an individualized spatial reference point (ISRP) of the ST segment can be constructed in each person, 2) the spatial variation of new measurements relative to the ISRP is less during physiological conditions than during acute CAO, and 3) the magnitude and direction of the shift vector can detect CAO and indicate the occluded artery.

Figure 17:
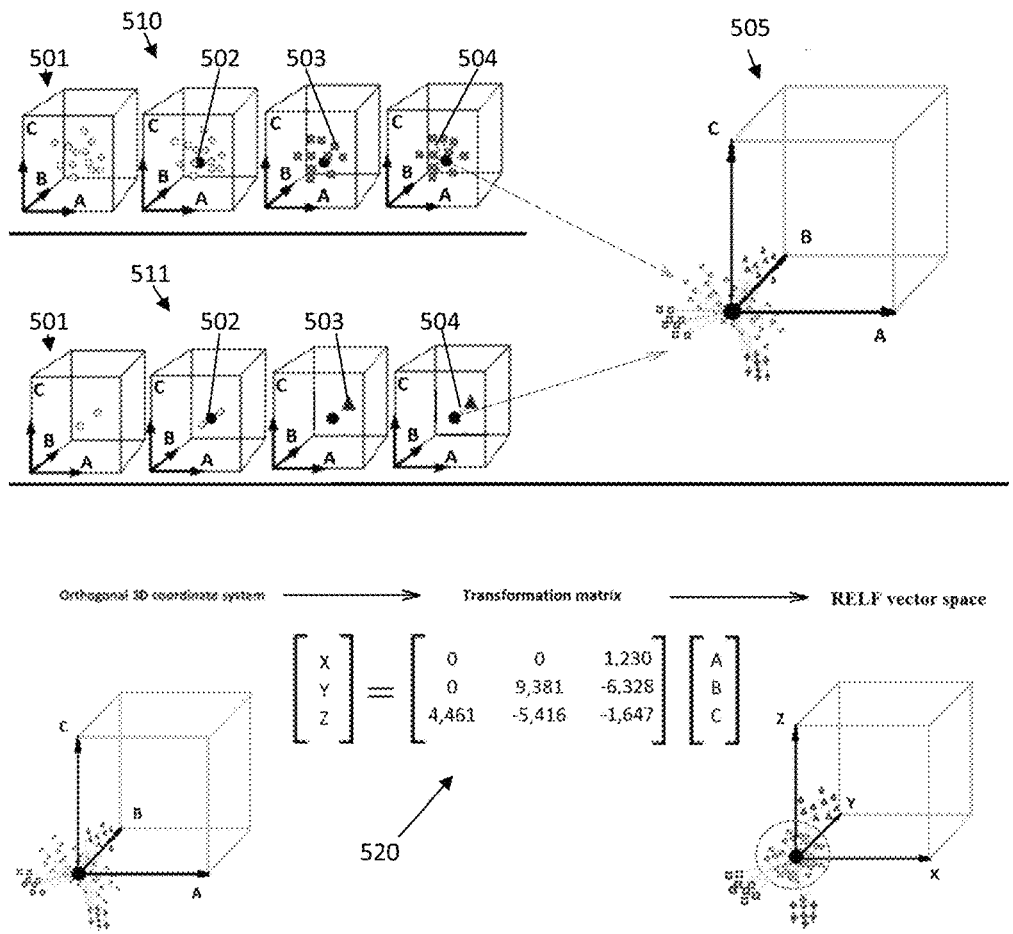
FIG. 17 shows detected ST amplitudes in three leads and the use of an individualized reference point in accordance with embodiments of the present invention.

FIG. 17 shows the detected ST amplitudes 501 in the three leads represented as coordinates in an orthogonal system (A,B,C). Thirteen reference measurements are spatially plotted in ABC, and an individualized ST reference point 502 was constructed from the average of all reference measurements. New measurements 503 are shown in the orthogonal system and ST shift vectors 504 relative to the ISRP are also shown. Results are shown separately for healthy subjects 510 and patients with CAO. The shift vectors are also shown centered 505 at the origin of the ABC coordinate system. Furthermore, an empirical transformation matrix 520 of the orthogonal system ABC into an orthogonal XYZ coordinate system until optimal discrimination of healthy subjects from patients with CAO in shown in FIG. 17. In this transformed vector space the magnitude of the ST shift vector of occlusions are maximally differentiated from the physiological shifts and therefore, can discriminate healthy subjects from patients with CAO. The transformed space will be further referred to as the RELF vector space and described by the orthogonal XYZ coordinates.

Referring to FIG. 9, in the present example, the ISRP of the ST segment in the CAO group was constructed from 2 measurements 203 recorded in supine and rest position on the catheterization table prior to the procedure, with a time interval of 2 to 10 minutes. It is to be noticed that theoretically a single measurement also could be sufficient. The average spatial position of these 2 measurements was defined as the ISRP 204 for the patient. For the healthy subjects, the ISRP of the ST segment was constructed from 13 consecutive measurements recorded during supine position, standing position, and immediately after at least 10 standing genuflexions (5, 3, and 5 measurements respectively). The average spatial position of these 13 measurements 201 was defined as the ISRP 202 for the healthy subject.

An ST shift vector 205 may be defined as the vector between the IRSP and any spatial ST point of interest, as also shown in FIG. 9. In the CAO group, the ST shift vector 206 was constructed after a measurement at 60 s of balloon inflation, or earlier in case of severe symptoms or presence of a large ST deviation during balloon inflation. The CAO group comprises occlusion events in the left anterior descending coronary artery LAD, circumflex coronary artery CX, and right coronary artery RCA.

In healthy subjects, 13 ST shift vectors 205 were constructed for 13 new measurements. Time interval between the IRSP measurement and the new measurement varied among subjects from one week to three months. The new measurements included consecutively five measurements in resting supine position, three measurements in standing position, and five measurements after several genuflexions.

The ST shift vectors of the healthy subjects and CAO group were projected onto a classifying system, e.g. an anatomical coordinate system although not limited thereto, shown in FIG. 10. The classifying coordinate system was empirically determined by rotating the lead1, lead2, and lead3 axis and changing the axis sensitivities to optimally discriminate the ST shift vectors of healthy subjects from the CAO group. The magnitude of the ST shift vectors in this classifying coordinate system was used as a discriminatory variable. The highest magnitude of the healthy subjects in the learning dataset was selected as the cut-off to discriminate the two groups.

To visualize the ST shift vectors in an anatomical reference system the vectors were transformed to fit in the Frank torso model. Furthermore, to separate in space the normal ST shift vectors of healthy individuals from those induced by coronary occlusion, a transformation matrix was derived with the learning data set and tested the matrix prospectively with the validation data set. In the training data set the ST shift vectors (n=195) of the healthy subjects and of the CAO group (n=30) were centred in the origin of orthogonal ABC coordinate system. The ABC space was empirically skewed and scaled to a space to achieve good discrimination of the ST-shift vectors of healthy subjects from those of the CAO group. To do so, the ABC coordinate system is transformed by skewing the angles between A, B and C (non-orthogonal skewing transformation) and by scaling of respectively A, B and C (scaling transformation). The optimal transformed data space is referred to as the RELF space and is described with an orthonormal XYZ system by the transformation matrix shown in FIG. 17. The magnitude of the ST shift vectors in the RELF space (XYZ) was used to discriminate ST shift vectors of healthy individual from those of the CAO group. The direction of the ST-shift vectors in the YZ plane was used to identify the culprit artery (left anterior descending artery (LAD) versus circumflex artery (CX) versus right coronary artery (RCA).

For each recording there was a simultaneous recording with the standard 12 leads ECG. The ECGs were assessed by two experts individually for the presence of ST elevation criteria according to the third international definition of myocardial infarction criteria. In case of mismatch, the assessment of a third expert was taken. In summary, ST elevation criteria were positive if in at least two consecutive leads from a standard 12 lead ECG the ST segment was elevated 1 mm or more. If V2 or V3 was taken into account the minimum elevation was 1.5 mm for women and 2 mm for men. If V2 or V3 was taken into account the minimum elevation was 1.5 mm for women and 2 mm for men. The ST level was measured at the J-point with respect to the PR-interval. Consecutive leads were defined as at least two out of the following sets: (II, III, and aVF); (I, aVL, and V6); (V1-V5). The ECGs from both groups were randomized and experts were blinded to the subject group.

In the CAO group, nine patients were excluded due to absence of any ECG changes during 1 minute of occlusion. In total, 60 ECG recordings from 51 patients with 60 CAOs and 390 ECG recordings from 30 healthy persons were included and analysed.

Figure 11:
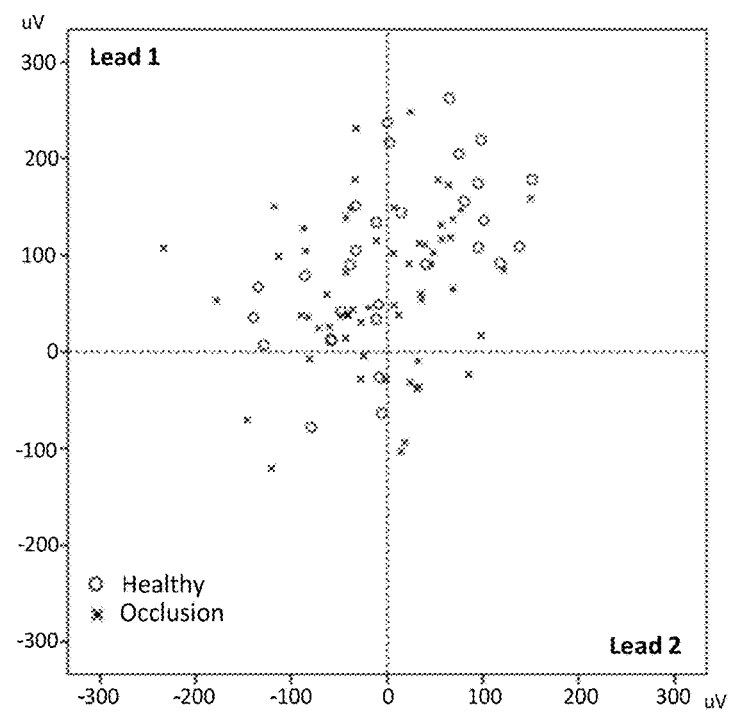
FIG. 11 shows the inter-individual variation of the ST reference point in the healthy and the PTCA group for an example illustrating embodiments of the present invention.
Figure 11:
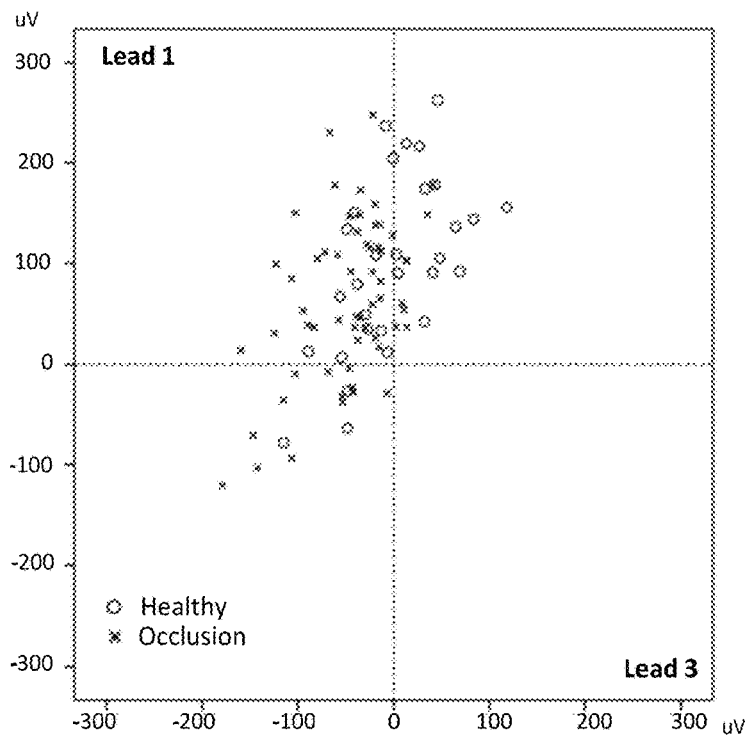

FIG. 11 shows the inter-individual variation of the ST reference point in the healthy and the PTCA group. In the healthy group the ST reference ranged from −80 to 260 μV, −150 to 150 μV, and −110 to 130 μV in leads 1, 2 and 3 respectively. In the PTCA group, the average reference ranged from −120 to 240 μV, −250 to 150 μV, and −180 to 4 μV in leads 1, 2 and 3 respectively. No significant difference was present in the ST reference between the healthy group and the PTCA group in any of the leads (mean±SD in lead 1=99.9±85 vs. 65.2±79.0 μV; lead 2=6.4±80.2 vs. −10.2±72.8 μV; lead 3=−0.5±51.8 vs. −48.2±48.1 μV, p=N.S. for all).

Figure 12:
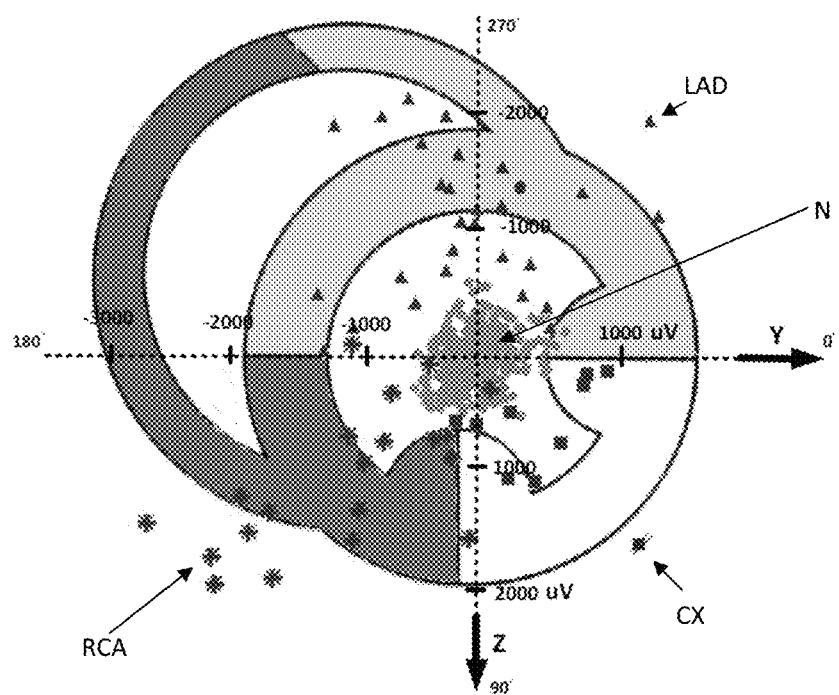
FIG. 12 shows projections of the ST shift vectors on the Y-Z plane after the basis transformation illustrated in FIG. 10, superimposed on the short axes view of echocardiography, for an example illustrating embodiments of the present invention.

The orthogonal system of lead1, lead2 and lead3 was transformed to an classifying coordinate system to discriminate ST shift vectors of healthy subjects from the CAO group. The Y-Z plane of the classifying coordinate system and the distribution of the ST shift vectors are shown in FIG. 12. The ST shift vectors from healthy subjects are centred in the plane, whereas the ST shift vectors of the CAO group are distributed in the periphery of the plane. Moreover, the ST shift vectors of the CAO group are clustered according to the territory of the occluded vessel. All occlusions in the left anterior descending artery (LAD) were distributed clockwise from the Y axis between 0 and 180 degrees. In the right coronary artery, 20 out of 22 occlusions were distributed clockwise between 180 and 270 degrees. In the left circumflex, 9 out of 10 occlusions were distributed clockwise between 270 and 360 degrees.

In contrast to the Y and Z axis, the X axis of the classifying coordinate system was less sensitive to ST shift vector; consequently, the Y-Z plane was designated as the coronary plane. The coronary plane corresponded to the standard short axis view in echocardiography. FIG. 12 shows the superimposition of the short axis view on the coronary plane with ST vector shift of the healthy subjects and CAO group.

The magnitude of the ST shift vectors in the spatial classifying coordinate system was used to discriminate the normal ST shift vectors (healthy individuals) from those induced by coronary occlusion, e.g. to detect occlusions. Overall, there was significant difference between the magnitude in healthy subjects and the CAO group (mean±SD=268±130 μV vs. 1439±856 μV; p<0.0001). The following table shows the detailed statistics of ST shift vector magnitude in every dataset and group. The ROC-curve for the validation data sets has an area under the curve of 0.963 (95% confidence interval, 0.921 to 1.000).

| Dataset | Group | Mean | SD | Min. | Max. | Median | p within set | p between sets |
|---|---|---|---|---|---|---|---|---|
| Learning | Healthy | 238.92 | 117.85 | 15.98 | 600.68 | 240.66 | | <0.0001 |
| | Occlusion | 1487.67 | 901.02 | 742.36 | 4832.05 | 1213.81 | <0.0001 | |
| Validation | Healthy | 296.88 | 134.54 | 48.94 | 679.24 | 280.25 | | |
| | Occlusion | 1390.54 | 820.20 | 229.70 | 3344.26 | 1236.72 | <0.0001 | 0.664 |
| Overall | Healthy | 267.75 | 129.55 | 15.98 | 679.24 | 263.52 | | |
| | Occlusion | 1439.11 | 855.63 | 229.70 | 4832.05 | 1213.81 | <0.0001 | |

Figure 13:
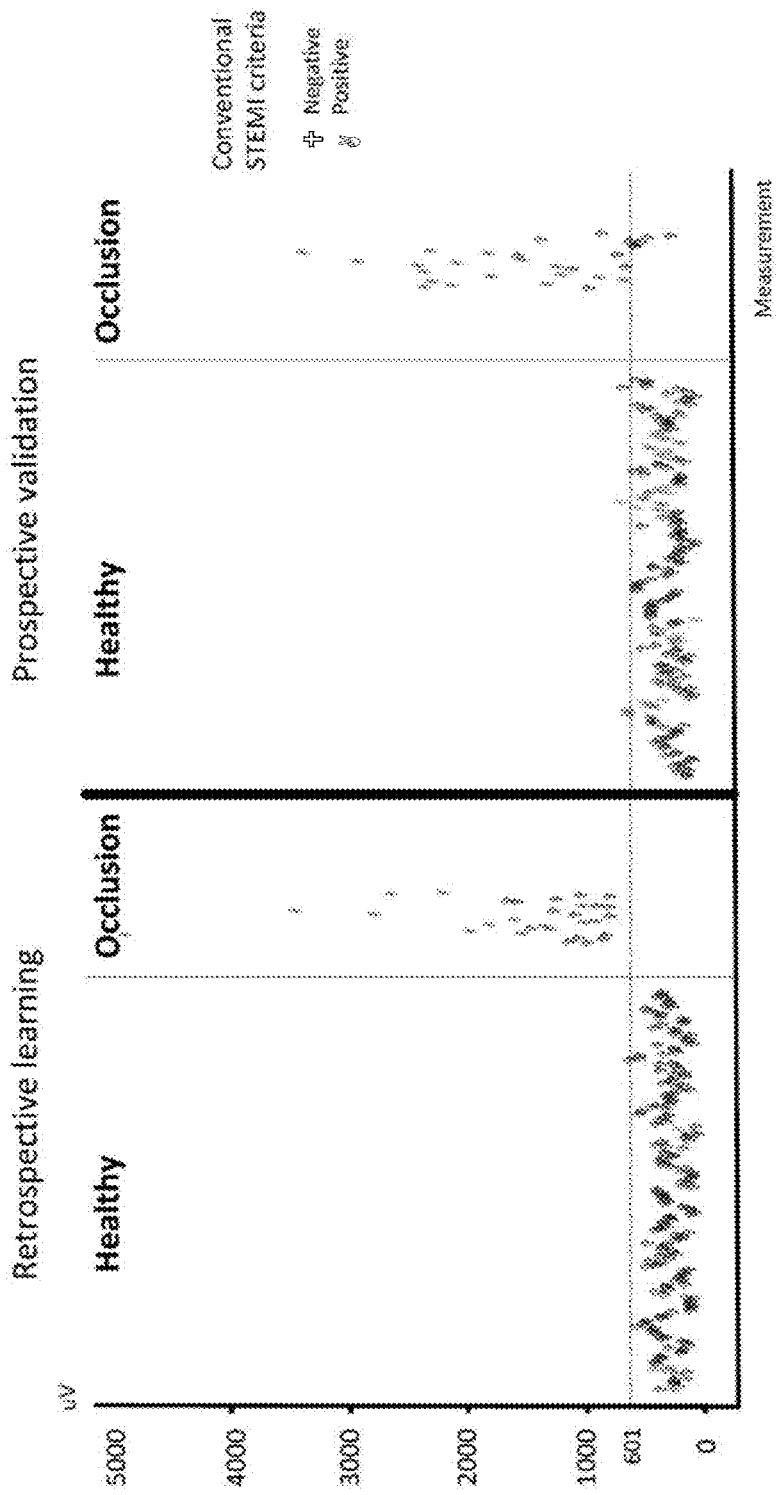
FIG. 13 shows a scatter plot of the magnitude of ST shift vectors in healthy and occlusion subjects in learning and validation datasets, in an example according to embodiments of the present invention.

FIG. 13 shows a plot of the ST shift vector magnitudes for every subject in the learning (left panel) and validation (right panel) datasets. In the learning dataset, the cut-off to discriminate healthy subjects from the CAO group was set at 601 µV (maximum magnitude in healthy subjects). In the prospective validation dataset, 191 out of 195 (97.9%) healthy subjects and 24 out of 30 (80%) CAO were correctly detected with this cut-off. All of the 6 CAO that were misclassified by the method were also negative according to the STEMI criteria.

Figure 14:
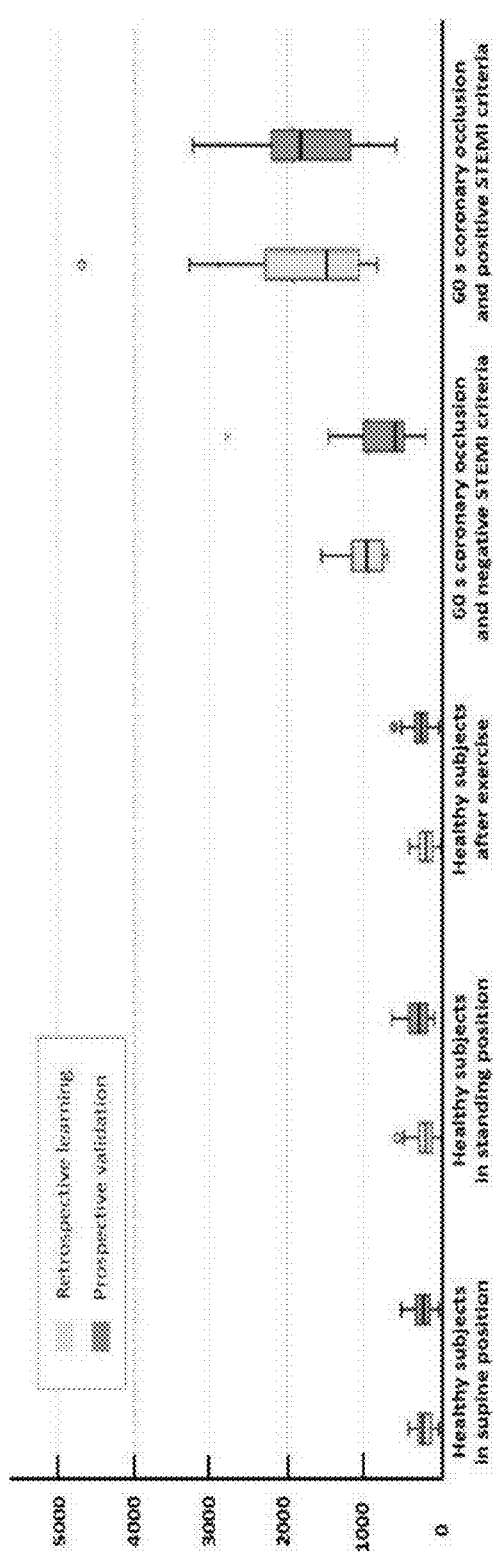
FIG. 14 shows boxplots of the magnitudes of the ST-shift vectors in learning dataset and validation set of healthy subjects and patients in an example according to embodiments of the present invention.

FIG. 14 shows a box plot of the magnitude of the ST shift vector in the learning and validation datasets. Body position and small exercise did not influence the magnitude in healthy subjects. The magnitude in the CAO group was significantly higher than in healthy subjects. This holds true even for a subgroup of CAO patients where the balloon inflation did not result in positive STEMI criteria on the standard 12 leads ECG.

The performance of the ST shift vector method was compared to the performance of the STEMI criteria on the conventional 12 leads ECG, as shown in the table herebelow. In the prospective validation dataset, the ST shift vector method was highly accurate (96%) and precise (positive predictive value=86%) compared to the STEMI criteria (72% and 26% respectively) to discriminate healthy subjects from patients after 60 s of occlusion. The RELF method, including the lead configuration, the algorithms and the empirical coordinate system for the ST shift vector, was compared to the STEMI criteria on the conventional 12 leads ECG. To dichotomize the decision variable (magnitude of ST shift vector in the XYZ coordinate system), as cut-off value the 97.5 percentile of the healthy subjects in the learning data set (486.7 microV) was used. In the prospective validation dataset, the RELF method showed a higher sensitivity compared to the conventional 12 lead ECG (27/30, 90% vs. 31/60, 51%, p<0.0001) whereas the specificity in healthy subjects was comparable (174/193, 90% vs. 331/390, 85%, p=0.48). The RELF method additionally specified the site of occlusion correctly in 55/58 (95%) (left anterior descending artery 28/28, right coronary artery 18/20 and circumflex artery 9/10).

|  | ST shift vector | | | STEMI criteria | | |
| --- | --- | --- | --- | --- | --- | --- |
|  | Occlusion | Healthy | Total | Occlusion | Healthy | Total |
| Learning | | | | | | |
| Positive | 30 | 0 | 30 | 14 | 10 | 24 |
| Negative | 0 | 195 | 195 | 16 | 185 | 201 |
| Total | 30 | 195 | 225 | 30 | 195 | 225 |
| Accuracy | | | 100% | | | 88% |
| Precision | | | 100% | | | 58% |
| Sensitivity | | | 100% | | | 47% |
| Specificity | | | 100% | | | 95% |
| Validation | | | | | | |
| Positive | 24 | 4 | 28 | 17 | 49 | 66 |
| Negative | 6 | 189 | 195 | 13 | 146 | 159 |
| Total | 30 | 193 | 223 | 30 | 195 | 225 |
| Accuracy | | | 96% | | | 72% |
| Precision | | | 86% | | | 26% |
| Sensitivity | | | 93% | | | 52% |
| Specificity | | | 91% | | | 85% |

In this example, a method for self-assessment and early detection of acute coronary artery occlusion according to embodiments of the present invention is validated. A 3-lead configuration with dedicated algorithm and coordinate system may discriminate physiological ST variations in healthy persons from ST changes induced by a one minute coronary artery occlusion. Surprisingly, the introduced method, while requiring only 3 lead ECG data, can be more accurate and precise than the STEMI criteria on the standard 12 lead ECG to detect early acute coronary occlusion. Moreover, the method may prospectively localize the coronary territory of the culprit vessel indicating that the methodology is also anatomically plausible.

Compared to STEMI criteria on the standard 12 lead ECG, this method may be more accurate and precise because it evaluates the spatial ST shift from an individualized spatial reference point (ISRP) rather than the isoelectric baseline of the ECG. In healthy subjects and in patients with coronary artery disease, the ST level in a non-ischemic state may not always be at the ECG isoelectric level and may therefore be subjected to incorrect interpretation. The present method is based on the shift of ST level relative to the individuals' reference level and therefore, not influenced by the inter-individual variations of ST levels.

A method for a 3-lead system that can discriminate physiological ST level variations in healthy persons from ST changes induced by a one minute coronary artery occlusion results in a surprisingly advantageous system. Even known system from the state of the art with a small number of leads, e.g. the Frank lead system consisting of 7 leads, typically are not self-applicable.

A high accuracy and precision may be achieved by a method as described in this example, which is assisted by three different factors. First, the lead configuration uses a new lead (VE minus VR) which shows small variations of ST levels in healthy persons. Second, a coordinate system dedicated to detect acute coronary artery occlusions equally sensitive for the three coronary territories is used, giving more weight to ST shifts vector in the short axis of left ventricle (Y and Z axis, coronary plane) compared to ST shifts vector in the long axis of the left ventricle (X-axis). Third, a method to determine the individualized spatial reference point (ISRP) is used. It is an advantage of embodiments of the present invention that not only a single reference measurement in supine position is used to set the individuals' spatial reference, but that variations due to body position and heart rates are taken into account to set the reference.

To summarize, the first example presented hereinabove relates to a method for analyzing electrocardiogram data in accordance with embodiments of the present invention that comprises obtaining a temporal sequence of electrocardiogram data registered by a plurality of electrodes corresponding to a plurality of predetermined locations on the body of a user. This exemplary method may particularly quantify inter- and intra-individual ST dipole variations in a human subject using an ECG system, e.g. a three-lead ECG system. In this example, a temporal sequence of electrocardiogram data may be obtained using a three-lead system, e.g. by carrying out three bipolar electrical measurements at three corresponding predetermined regions on the surface of the body. Each such bipolar electrical measurement may comprise an electric potential difference measurement between a point on the surface of the body in the corresponding predetermined region at one hand and a point on the surface of the body in a reference region. For example, the reference region may correspond to the right arm, or a predetermined part thereof, such as the right hand or a finger on the right hand, e.g. the right index finger or the right thumb. For example, the electrocardiogram data may comprise a first bipolar measurement between a chest electrode point VE on the body, located between 3 cm and 6 cm above the fourth left parasternal intercostal space, and the right shoulder VR, a second bipolar measurement between the left crista iliaca VF and the right shoulder VR, and a third bipolar measurement between the left shoulder VL and right shoulder VR.

The method of this example further comprises determining at least one parameter indicative of a morphological feature from the temporal sequence of electrocardiogram data. This at least one parameter may comprise, or consist of, three ST levels determined from the three bipolar electrical measurements respectively, e.g. three ST levels forming a three-dimensional coordinate representation of the ST dipole, e.g. such that the morphological feature comprises a multi-dimensional ST segment feature. The method according to this example further comprises performing a comparison of the at least one parameter to a previously determined distribution of the at least one parameter obtained from the user under a plurality of predetermined physiological conditions. The at least one parameter may be compared to the previously determined distribution by calculating a difference vector of the three ST levels with respect to a reference vector. This reference vector, e.g. a reference ST dipole vector, may be obtained by calculating an average of a plurality of dipole measurements under at least three different, predetermined physiological conditions, for example an average of 13 ST dipole vector measurements obtained for three different physiological conditions. Each of these dipole measurements may be obtained using the same process as for determining the temporal sequence of electrocardiogram data, e.g. using the three-lead system comprising three bipolar electrical measurements at the corresponding three predetermined regions on the surface of the body. The at least one parameter may thus be compared to the personalized reference distribution, e.g. by subtracting the stored mean value such that a shift vector, e.g. the difference vector, is obtained.

The exemplary method also comprises generating a signal taking into account this comparison, for example a signal representative of a risk of a myocardial infarction occurring in the body of the user. This exemplary method has been successfully applied for detecting an acute coronary occlusion. It has been observed that the intra-individual variation of the difference vector, e.g. the difference of the three ST levels with respect to the reference vector, when caused by an acute occlusion is larger than the intra-individual variations occurring over time under normal conditions, e.g. in the absence of an acute occlusion condition, for example over a time period of two or more months, as well as larger than the intra-individual variations occurring due to varying physiological conditions. This exemplary method may be more sensitive and specific for acute coronary occlusion detection than, for example, a stationary 12-lead electrocardiogram as known in the art. In this example, generating the signal representative of the risk of a myocardial infarction occurring in the body takes a further distribution of the at least one parameter into account, in which this further distribution characterizes the distribution of the shift vector in a population of reference individuals, e.g. in which the further distribution is obtained from a population of reference individuals, such as group having the same gender and/or being in a same age group as the user. This further distribution may be taken into account by applying a population-specific variance or covariance, e.g. in order to normalize the at least one parameter to a population reference variance or covariance or to adjust a detection threshold, e.g. a radius to be exceeded by the at least one parameter, for generating the signal indicating an acute occlusion condition.

Figure 18:
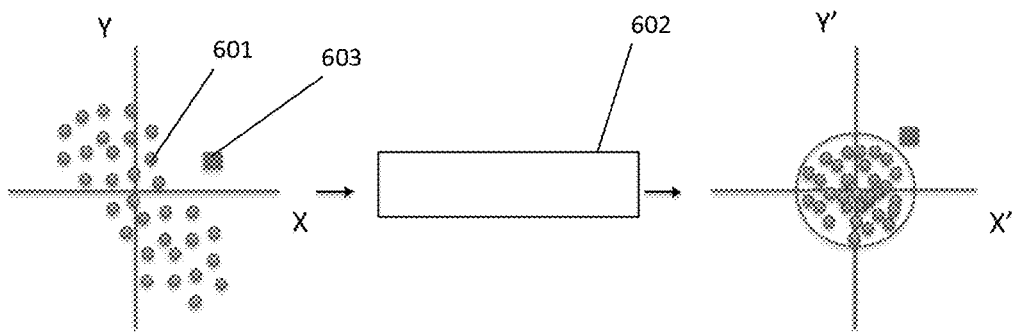
FIG. 18 schematically illustrates features of a method according to a first example of embodiments of the present invention.

Particular aspects of the method according to this example is schematically shown in FIG. 18. For simplicity, only axes X and Y, respectively X' and Y' are shown in FIG. 18, even though the ST shift vectors have three components X, Y, Z in accordance with this example. The set ST shift vectors 601 obtained for different healthy individuals was used to determine an ortho-normalized coordinate basis using principal component analysis. This transformation 602 projects the at least one parameter (X, Y, Z), in which X represents the ST level over the bipolar lead RE minus the individual reference ST level over the bipolar lead RE, Y represents the ST level over the bipolar lead RL minus the individual reference ST level over the bipolar lead RL, and Z represents the ST level over the bipolar lead RF minus the individual reference ST level over the bipolar lead RF, onto an ortho-normalized coordinate system X', Y', Z'. This example shows that this transformation 602 is able to successfully separate an abnormal ST dipole shift vector 603 of a subject A, e.g. corresponding to an acute coronary occlusion condition, from the set of samples obtained from healthy individuals. The further example provided hereinbelow illustrate exemplary methods of carrying out the invention in accordance with embodiments of the present invention. These examples are intended for illustrating various aspects of the present invention, without being intended to limit the invention in any way to the particular examples set forth.

A second example also relates to a method for analyzing electrocardiogram data that comprises obtaining the temporal sequence of electrocardiogram data, analogous to the description of the first example hereinabove. The method of this example also comprises determining at least one parameter indicative of a morphological feature, e.g. comprising or consisting of the three ST levels determined from the three bipolar electrical measurements respectively. The method according to this example also comprises performing a comparison of the at least one parameter to a previously determined distribution of the at least one parameter obtained from the user under a plurality of predetermined physiological conditions, e.g. by a difference vector of the three ST levels with respect to a reference vector obtained as an average of a plurality of dipole measurements under at least three different, predetermined physiological conditions. This exemplary method also comprises generating a signal representative of a risk of a myocardial infarction occurring in the body of the user. However, unlike in the first example hereinabove, where generating the signal representative of the risk of a myocardial infarction occurring in the body takes a further distribution into account that characterizes the shift vector in a population of reference individuals, in this example, sufficient subject-specific previous measurements under normal conditions, e.g. in the absence of an acute occlusion condition, are gathered such that a subject-specific variance or covariance representative of a normal condition can be applied, e.g. in order to normalize the at least one parameter to a population reference variance or covariance or to adjust a detection threshold, e.g. a radius to be exceeded by the at least one parameter, for generating the signal indicative for an acute occlusion condition. However, in a particularly advantageous embodiments, additional data may be gathered periodically for improving the statistical quality of the previously determined distribution of the at least one parameter obtained from the user under a plurality of predetermined physiological conditions. A population-specific further distribution as described in the first example hereinabove may be taken into account until the gathered data from the user is significantly different from the reference distribution, e.g. using a statistical test as known in the art, for example a Z-test, a Student t-test, an F-test or a Kolmogorov-Smirnov test. Thus, a method according to the first example hereinabove may be applied until the subject-specific gathered data show a significant divergence of the distribution of the at least one parameter for the specific user under normal, e.g. non-acute, conditions from the distribution of the at least one parameter for a reference population of individuals under normal, e.g. non-acute, conditions.

Figure 19:
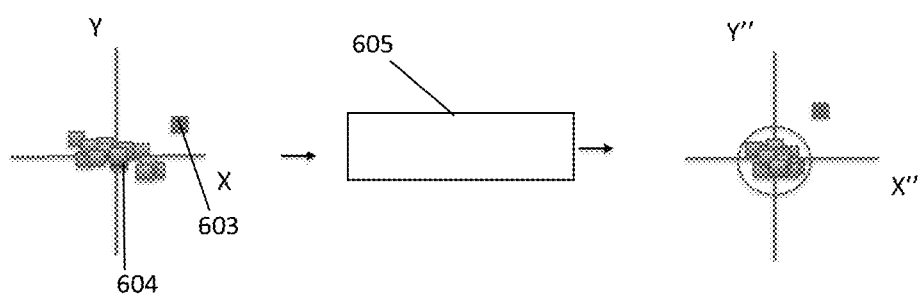
FIG. 19 schematically illustrates features of a method according to a second example of embodiments of the present invention.

This exemplary method was tested on the same database as described hereinabove. 25 measurements were used for each human subject to obtain a person-specific distribution. Features of this method are illustrated by FIG. 19. For simplicity, only axes X and Y, respectively X" and Y" are shown in FIG. 19, even though the ST shift vectors have three components X, Y, Z in accordance with this example. The set of ST shift vectors 604 obtained for an individual A under normal, e.g. healthy, circumstances was used to determine an ortho-normalized coordinate basis using principal component analysis. A differently shaped distribution of the intra-subject samples under normal condition can be seen, when compared with the inter-subject samples shown in FIG. 18. For subject A, and similarly for each other individual to which the method is applied, a principal component analysis was applied, e.g. independently from that obtained for the other subjects, to the at least one parameter (X, Y, Z), in which X represents the ST level over the bipolar lead RE minus the individual reference ST level over the bipolar lead RE, Y represents the ST level over the bipolar lead RL minus the individual reference ST level over the bipolar lead RL, and Z represents the ST level over the bipolar lead RF minus the individual reference ST level over the bipolar lead RF. Thus, a transformation 605 is determined that projects the at least one parameter (X, Y, Z) onto an ortho-normalized coordinate system X", Y", Z". This example shows that this transformation 605 is able to successfully separate an abnormal ST dipole shift vector 603 of the subject A, e.g. corresponding to an acute coronary occlusion condition, from the set of ST shift vectors 604 obtained for an individual A under normal, e.g. healthy, circumstances. When the individualized ortho-normalizing transformation is applied to 60 shift vectors corresponding to acute coronary occlusion conditions, an increased sensitivity for detecting an occlusion was observed of 98%, compared to 95% when a population-based ortho-normalization was performed, in accordance with the first example provided hereinabove. Likewise, specificity increased from 94% to 98%. The numbers are obtained for a cutoff placed at the percentile 97.5 of the healthy in the learning database.

Thus, because the reference distribution is tuned to the individual response under normal conditions, e.g. only a set of ST dipole variations of the individual at hand is taken into account, the sensitivity and specificity of the detection method may be increased. However, this method in accordance with this second example may require that sufficient reference measurements of the individual at hand are available to define a distribution that is significantly different of a reference distribution obtained over a set of healthy individuals, e.g. in accordance with the first example presented hereinabove. In an implementation of a method in accordance with embodiments of the present invention, a test may be performed each time new data for a subject is acquired, e.g. such as to switch from a population-based method such as described in the first example hereinabove to a subject-specific method such as described in the present example.

In the table presented hereinbelow, a comparison is made between the methods of both examples discussed hereinabove and a prior art method based on a standard 12-lead electrocardiogram (ECG). The first and second example are respectively designated the acronyms RELF-2 and RELF-3. AUC indicates the area under the Receiver Operating Characteristic (ROC) curve. The 95% confidence interval (CI) on the AUC is also reported. The number of samples in the test set corresponding to normal conditions (e.g. healthy) are indicated by $n_-$, while $n_+$ indicates the number of samples in the test set corresponding to the acute coronary occlusion condition.

|  | ECG | RELF-2 | RELF-3 |
|---|---|---|---|
| $N_r$ | 0 | 13 | 25 |
| Sensitivity | 85% | 95% | 98.1% |
| Specificity | 52% | 94% | 97.9% |
| $n_-$ | 388 | 388 | 772 |
| $n_+$ | 60 | 60 | 1798 |
| AUC |  | 0.98 | 0.998 |
| 95% CI |  | 0.97-0.99 | 0.997-0.999 |

The invention claimed is:

1. A device for analyzing electrocardiogram data, the device comprising:
an input means for obtaining a temporal sequence of electrocardiogram data registered by at least 2 electrodes corresponding to a plurality of predetermined locations on the body of a user,
a processing unit connected to said input means to receive and process the temporal sequence of electrocardiogram data, the processing unit being programmed for determining at least one parameter indicative of a morphological feature of said temporal sequence of electrocardiogram data, the morphological feature comprising a multi-dimensional ST segment feature, and for performing a comparison of said at least one parameter to a previously determined distribution of said at least one parameter, the previously determined distribution being obtained from said user under a plurality of different physiological conditions; and
an output means connected to said processing unit for generating a signal taking into account said comparison, the signal being representative of a risk of a myocardial infarction occurring in said body.

2. The device according to claim 1, wherein the electrocardiogram data registered by at least 2 electrodes corresponding to a plurality of predetermined locations on the body of a user comprises a first bipolar measurement obtained between a chest electrode point on the body located between 3 cm and 6 cm above the fourth left parasternal intercostal space and a location on the right upper extremity.

3. The device according to claim 2, wherein the electrocardiogram data registered by at least 2 electrodes corresponding to a plurality of predetermined locations on the body of a user furthermore comprises a second bipolar measurement obtained between the left crista iliaca and the location on the right upper extremity, and a third bipolar measurement obtained between a location on the left upper extremity and the location on the right upper extremity.

4. The device according to claim 1, wherein said device is furthermore adapted for prompting a user for inputting during a calibration and/or re-calibration procedure a temporal sequence of electrocardiogram data registered by a plurality of electrodes corresponding to the plurality of predetermined locations on the body of the user obtained under a plurality of different physiological conditions.

5. The device according to claim 4, wherein the processing unit is furthermore adapted for deriving an updated distribution of said at least one parameter based on said temporal sequence inputted during a re-calibration procedure.

6. The device according to claim 4, wherein the processing unit is adapted for performing said comparison of said at least one parameter to said previously determined distribution by subtracting an average of said at least one parameter obtained from said user under a plurality of different physiological conditions, corresponding to said previously determined distribution, to obtain a shift vector and for applying a coordinate transformation to said shift vector.

7. The device according to claim 6, wherein the processing unit is furthermore adapted for applying said coordinate transformation to said shift vector, wherein said coordinate transformation is determined by a principal component analysis of a further distribution of the at least one parameter over a population of reference samples obtained from a plurality of different individuals.

8. The device according to claim 6, wherein the processing unit is furthermore adapted for applying said coordinate transformation to said shift vector, wherein said coordinate transformation is determined by a principal component analysis of said at least one parameter obtained from said user under a plurality of different physiological conditions corresponding to said previously determined distribution.

9. The device according to claim 1, wherein the device is a smartphone.

10. The device according to claim 1, wherein the at least one parameter is indicative of a multi-dimensional vector of ST segment features.

11. The device according to claim 1, wherein said different physiological conditions are different conditions of metabolic exertion.

12. A method for analyzing electrocardiogram data, the method comprising:
obtaining a temporal sequence of electrocardiogram data registered by a at least two electrodes corresponding to a plurality of predetermined locations on the body of a user,
determining at least one parameter indicative of a morphological feature of said temporal sequence of electrocardiogram data, the morphological feature comprising a multi-dimensional ST segment feature;
obtaining a previously determined distribution of said at least one parameter obtained from said user under at least two different physiological conditions;
performing a comparison of said at least one parameter to said previously determined distribution of said at least one parameter; and
generating a signal, representative of a risk of a myocardial infarction occurring in the body of the user, taking into account said comparison.

13. The method according to claim 12, wherein obtaining the temporal sequence of electrocardiogram data comprises obtaining electrocardiogram data using a measurement wherein a chest electrode point is located between 3 cm and 6 cm above the fourth left parasternal intercostal space on the body of the user.

14. A method according to claim 12, wherein obtaining a temporal sequence of electrocardiogram data comprises obtaining at least three time series of bipolar measurements, each of the time series being recorded consecutively.

15. The method according to claim 14, wherein the method comprises, prior to said obtaining of said temporal sequence of electrocardiogram data, updating the previously determined distribution of said at least one parameter obtained from said user under a plurality of different physiological conditions.

16. The method according to claim 15, wherein said updating comprises obtaining a temporal sequence of electrocardiogram data registered by a plurality of electrodes corresponding to a plurality of predetermined locations on the body of a user under a plurality of different physiological conditions, as prompted.

17. The method according to claim 12, wherein obtaining the temporal sequence of electrocardiogram data comprises obtaining the temporal sequence of electrocardiogram data, in which the electrocardiogram data comprises a first bipolar measurement between a chest electrode point and the right shoulder, a second bipolar measurement between the left crista iliaca and the right shoulder, and a third bipolar measurement between the left shoulder and right shoulder.

18. The method according to claim 12, wherein performing said comparison comprises subtracting from the at least one parameter an average of said at least one parameter obtained from said user under said at least two different physiological conditions, corresponding to said previously determined distribution of said at least one parameter, to obtain a shift vector, and applying a coordinate transformation to said shift vector.

19. The method according to claim 18, wherein applying said coordinate transformation to said shift vector comprises determining said coordinate transformation by a principal component analysis of a further distribution of the at least one parameter over a population of reference samples obtained from a plurality of different individuals.

20. The method according to claim 18, wherein applying said coordinate transformation to said shift vector comprises determining said coordinate transformation by a principal component analysis of said at least one parameter obtained from said user under a plurality of different physiological conditions corresponding to said previously determined distribution.

21. The method according to claim 12, wherein said determining the at least one parameter comprises determining at least one value indicative of a morphological feature defined for a local time interval less than the duration of a representative heartbeat.

22. The method according to claim 12, wherein said determining the at least one parameter comprises determining at least one value indicative of a property of at least one ST segment in said temporal sequence of electrocardiogram data.

23. The method according to claim 12, wherein said determining at least one parameter comprises determining at least one value indicative of J-point elevation.

24. The method according to claim 12, wherein said determining at least one parameter comprises, for each subsequence corresponding to a single heartbeat in said temporal sequence, detecting a first fiducial marker in the ST segment and detecting a second fiducial marker in the PR segment, and calculating the difference in amplitude between the first fiducial marker and the second fiducial marker aggregated over a plurality of said subsequences.

25. A device for analyzing electrocardiogram data, the device comprising:

an input means for obtaining a temporal sequence of electrocardiogram data registered by at least 2 electrodes corresponding to a plurality of predetermined locations on the body of a user;

a processing unit connected to said input means to receive and process the temporal sequence of electrocardiogram data, the processing unit being programmed for determining at least one parameter indicative of a morphological feature of said temporal sequence of electrocardiogram data, the morphological feature comprising a multi-dimensional ST segment feature, and for performing a comparison of said at least one parameter to a previously recorded individual spatial reference of said at least one parameter obtained from said user under a plurality of different physiological conditions; and an output means connected to said processing unit for generating a signal taking into account said comparison, the signal being representative of a risk of a myocardial infarction occurring in said body;

wherein the processing unit is adapted for performing said comparison of said at least one parameter to said previously recorded individual spatial reference by subtracting an average of said at least one parameter obtained from said user under a plurality of different physiological conditions, corresponding to said previously recorded individual spatial reference, to obtain a shift vector and for applying a coordinate transformation to said shift vector.

* * * * *